(12) United States Patent
Rodrigues

(10) Patent No.: US 11,744,528 B2
(45) Date of Patent: Sep. 5, 2023

(54) ADAPTIVE COMPTON CAMERA FOR MEDICAL IMAGING

(71) Applicant: Siemens Medical Solutions USA, Inc., Malvern, PA (US)

(72) Inventor: Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 74 days.

(21) Appl. No.: 17/250,492

(22) PCT Filed: Aug. 7, 2018

(86) PCT No.: PCT/US2018/045469
§ 371 (c)(1),
(2) Date: Jan. 28, 2021

(87) PCT Pub. No.: WO2020/032924
PCT Pub. Date: Feb. 13, 2020

(65) Prior Publication Data
US 2021/0290196 A1    Sep. 23, 2021

(51) Int. Cl.
*A61B 6/00*  (2006.01)
*A61B 6/03*  (2006.01)
(Continued)

(52) U.S. Cl.
CPC ............ *A61B 6/037* (2013.01); *A61B 6/0407* (2013.01); *A61B 6/4233* (2013.01);
(Continued)

(58) Field of Classification Search
CPC ......... A61B 6/03; A61B 6/037; A61B 6/0407; A61B 6/42; A61B 6/4208; A61B 6/4233; A61B 6/4241; A61B 6/4258; A61B 6/4266; A61B 6/4275; A61B 6/44; A61B 6/4405; A61B 6/4411; A61B 6/4417; A61B 6/5282; A61B 6/0487; A61B 6/4225; G01T 1/24; G01T 1/242; G01T 1/243; G01T 1/249;
(Continued)

(56) References Cited

U.S. PATENT DOCUMENTS 4,700,074 A     10/1987  Bosnjakovic
5,093,575 A  *  3/1992   Perusek ............... G01T 1/1648
                                              250/363.08
(Continued)

FOREIGN PATENT DOCUMENTS

EP        2060932 B1    3/2017
JP      H11295425 A    10/1999
(Continued)

OTHER PUBLICATIONS

An English Translation of JP2008-232971 A by Patent Translate. (Year: 2022).*
(Continued)

*Primary Examiner* — Allen C. Ho

(57) ABSTRACT

To optimize an image quality and/or a sensitivity, a Compton camera is adaptable. A scatter detector and/or a catcher detector may move closer to and/or further away from a patient and/or each other. This adaptation allows a balancing of the image quality and the sensitivity by altering the geometry.

17 Claims, 12 Drawing Sheets

(51) Int. Cl.
*A61B 6/04* (2006.01)
*G01T 1/16* (2006.01)
*G01T 1/161* (2006.01)
*G01T 1/24* (2006.01)
*G01T 1/29* (2006.01)

(52) U.S. Cl.
CPC .......... *A61B 6/4258* (2013.01); *A61B 6/4266* (2013.01); *A61B 6/4275* (2013.01); *A61B 6/44* (2013.01); *A61B 6/4411* (2013.01); *A61B 6/4417* (2013.01); *A61B 6/4429* (2013.01); *A61B 6/5282* (2013.01); *G01T 1/16* (2013.01); *G01T 1/1603* (2013.01); *G01T 1/1606* (2013.01); *G01T 1/24* (2013.01); *G01T 1/242* (2013.01); *G01T 1/243* (2013.01); *G01T 1/249* (2013.01); *G01T 1/29* (2013.01); *G01T 1/2907* (2013.01); *G01T 1/2914* (2013.01); *G01T 1/2921* (2013.01); *G01T 1/2928* (2013.01); *G01T 1/2935* (2013.01); *G01T 1/2964* (2013.01); *G01T 1/2971* (2013.01); *G01T 1/2985* (2013.01)

(58) Field of Classification Search
CPC ....... G01T 1/29; G01T 1/2907; G01T 1/2914; G01T 1/2921; G01T 1/2928; G01T 1/2935; G01T 1/2964; G01T 1/2971; G01T 1/2985; G01T 1/16; G01T 1/1603; G01T 1/1606; G01T 1/248
USPC ...................... 378/19, 20, 62, 63, 98.8, 189; 250/363.01, 363.02, 363.03, 363.04, 250/363.05, 370.09
See application file for complete search history.

(56) References Cited

U.S. PATENT DOCUMENTS

| | | | |
|---|---|---|---|
| 5,097,131 A * | 3/1992 | Plummer | G21K 1/025 250/363.01 |
| 5,097,132 A * | 3/1992 | Plummer | A61B 6/037 250/363.08 |
| 5,206,512 A * | 4/1993 | Iwao | G01T 1/1648 250/363.04 |
| 5,757,006 A * | 5/1998 | DeVito | G01T 1/1642 250/363.04 |
| 5,821,541 A | 10/1998 | Tumer | |
| 6,184,530 B1 * | 2/2001 | Hines | A61B 6/037 250/363.04 |
| 6,323,492 B1 | 11/2001 | Clinthorne | |
| 6,346,706 B1 | 2/2002 | Rogers et al. | |
| 6,512,232 B2 * | 1/2003 | Pehl | G01T 1/2985 250/252.1 |
| 6,528,795 B2 * | 3/2003 | Kurfess | G01T 1/242 250/369 |
| 6,583,420 B1 * | 6/2003 | Nelson | A61B 6/4258 250/397 |
| 6,762,413 B2 | 7/2004 | Zeng | |
| 6,791,090 B2 * | 9/2004 | Lin | G01T 1/242 250/336.1 |
| 6,881,959 B2 * | 4/2005 | Meng | G01T 1/1642 250/366 |
| 6,987,836 B2 * | 1/2006 | Tang | G21K 1/025 378/154 |
| 7,015,477 B2 | 3/2006 | Gunter | |
| 7,045,789 B2 | 5/2006 | Ogawa et al. | |
| 7,147,372 B2 * | 12/2006 | Nelson | A61B 6/4233 378/207 |
| 7,262,417 B2 | 8/2007 | Smith | |
| 7,291,841 B2 * | 11/2007 | Nelson | G01T 1/243 250/370.08 |
| 7,304,309 B2 | 12/2007 | Suhami | |
| 7,321,122 B2 | 1/2008 | Bryman | |
| 7,345,283 B2 | 3/2008 | Gunter | |
| 7,412,022 B2 * | 8/2008 | Jupiter | G01N 23/046 378/82 |
| 7,504,635 B2 | 3/2009 | Ramsden | |
| 7,550,738 B1 | 6/2009 | DeVito | |
| 7,573,039 B2 | 8/2009 | Smith | |
| 7,635,848 B2 * | 12/2009 | Nelson | G01T 1/2008 250/370.11 |
| 7,667,203 B2 | 2/2010 | Hindi et al. | |
| 7,732,773 B2 * | 6/2010 | Mihailescu | G01T 1/2985 250/363.04 |
| 7,750,308 B2 * | 7/2010 | Shirahata | G01T 1/1642 250/370.09 |
| 7,831,024 B2 | 11/2010 | Metzler et al. | |
| 7,863,567 B1 | 1/2011 | Hynes et al. | |
| 7,928,399 B2 | 4/2011 | Myjak et al. | |
| 8,063,379 B2 * | 11/2011 | Suhami | G01T 5/02 250/370.09 |
| 8,076,645 B2 * | 12/2011 | Motomura | G01T 1/242 250/370.09 |
| 8,107,589 B2 | 1/2012 | Sakurai et al. | |
| 8,139,713 B2 * | 3/2012 | Janbakhsh | A61B 6/5235 378/19 |
| 8,153,986 B2 | 4/2012 | Mihailescu et al. | |
| 8,217,362 B2 | 7/2012 | DeVito | |
| 8,299,437 B2 | 10/2012 | Nakamura | |
| 8,354,648 B2 | 1/2013 | Laurent et al. | |
| 8,437,836 B2 * | 5/2013 | Gagnon | A61B 6/486 600/407 |
| 8,476,595 B2 | 7/2013 | McKinsey et al. | |
| 8,515,011 B2 | 8/2013 | Mundy et al. | |
| 8,519,343 B1 | 8/2013 | Mihailescu et al. | |
| 8,716,669 B2 | 5/2014 | Miyaoka et al. | |
| 8,742,360 B2 | 6/2014 | Yamaguchi et al. | |
| 8,785,864 B2 * | 7/2014 | Ricci | H01L 27/14663 250/367 |
| 8,847,166 B2 | 9/2014 | Fukuchi et al. | |
| 9,029,791 B1 * | 5/2015 | Kovalski | G06T 11/005 250/369 |
| 9,134,440 B2 * | 9/2015 | Sanuki | G01T 1/2928 |
| 9,192,346 B2 * | 11/2015 | Zingerman | A61B 6/4417 |
| 9,349,577 B2 * | 5/2016 | Cussonneau | G01T 1/2985 |
| 9,579,072 B1 * | 2/2017 | Grobshtein | G01T 1/2985 |
| 9,693,744 B2 * | 7/2017 | Rafaeli | A61B 6/4452 |
| 9,763,631 B2 * | 9/2017 | Hefetz | A61B 6/0407 |
| 10,143,437 B2 * | 12/2018 | Hefetz | A61B 6/52 |
| 10,249,891 B2 * | 4/2019 | Ikeuchi | H01M 8/04014 |
| 10,281,594 B2 * | 5/2019 | Benlloch Baviera | G01T 1/2002 |
| 10,371,834 B2 * | 8/2019 | Nelson | G01T 1/1611 |
| 10,502,844 B2 * | 12/2019 | Hugg | G01T 1/243 |
| 10,575,802 B2 * | 3/2020 | Bouhnik | A61B 6/4291 |
| 10,884,139 B2 * | 1/2021 | Polf | G01T 1/2985 |
| 11,426,135 B2 * | 8/2022 | Vija | A61B 6/4275 |
| 11,647,973 B2 * | 5/2023 | Vija | A61B 6/4488 600/436 |
| 2002/0008205 A1 | 1/2002 | Kurfess et al. | |
| 2002/0134942 A1 | 9/2002 | Pehl et al. | |
| 2003/0161526 A1 | 8/2003 | Jupiter et al. | |
| 2004/0084624 A1 | 5/2004 | Meng et al. | |
| 2004/0251419 A1 | 12/2004 | Nelson et al. | |
| 2005/0139775 A1 | 6/2005 | Gono et al. | |
| 2005/0253073 A1 | 11/2005 | Joram et al. | |
| 2007/0253530 A1 | 11/2007 | Mihailescu et al. | |
| 2008/0088059 A1 | 4/2008 | Tang et al. | |
| 2008/0139914 A1 | 6/2008 | Gaved et al. | |
| 2009/0202041 A1 | 8/2009 | Shirahata et al. | |
| 2010/0090117 A1 | 4/2010 | Nelson | |
| 2010/0294945 A1 | 11/2010 | Cussonneau | |
| 2011/0303854 A1 | 12/2011 | DeVito | |
| 2012/0043467 A1 | 2/2012 | Gueorguiev et al. | |
| 2012/0132814 A1 | 5/2012 | Weinberg | |
| 2012/0217386 A1 | 8/2012 | Ricci et al. | |
| 2012/0290519 A1 | 11/2012 | Fontaine et al. | |
| 2014/0110592 A1 | 4/2014 | Nelson et al. | |
| 2015/0331115 A1 | 11/2015 | Nelson et al. | |
| 2017/0012308 A1 | 1/2017 | Ikeuchi | |

(56) References Cited

U.S. PATENT DOCUMENTS

2017/0285191 A1    10/2017  Hugg et al.
2021/0282725 A1*    9/2021  Rodrigues ................. G01T 1/29
2021/0290189 A1*    9/2021  Vija ..................... A61B 6/4411

FOREIGN PATENT DOCUMENTS

| JP | 2008232971 A | 10/2008 |
| JP | 2013022041 A | 2/2013 |
| JP | 2013033009 A | 2/2013 |
| JP | 2014149308 A | 8/2014 |
| JP | 2017026423 A | 2/2017 |

OTHER PUBLICATIONS

Soo Mee Kim et al., Fully three-dimensional OSEM-based image reconstruction for Compton imaging using optimized ordering schemes, Physics in Medicine and Biology 55, 5007-5027, 2010. (Year: 2010).*

Hee Seo et al., AID A Novel Method for Improving the Imaging Resolution of a Table-Top Compton Camera, IEEE Transactions on Nuclear Science, vol. 55, No. 5, Oct. 2008. (Year: 2008).*

Ordonez, Caesar E., Alexander Bolozdynya, and Wei Chang. "Doppler broadening of energy spectra in Compton cameras." Nuclear Science Symposium, 1997. IEEE. vol. 2. IEEE, 1997.

International Search Report for Corresponding International Application No. PCT/US2018/045469, dated May 16, 2019.

* cited by examiner

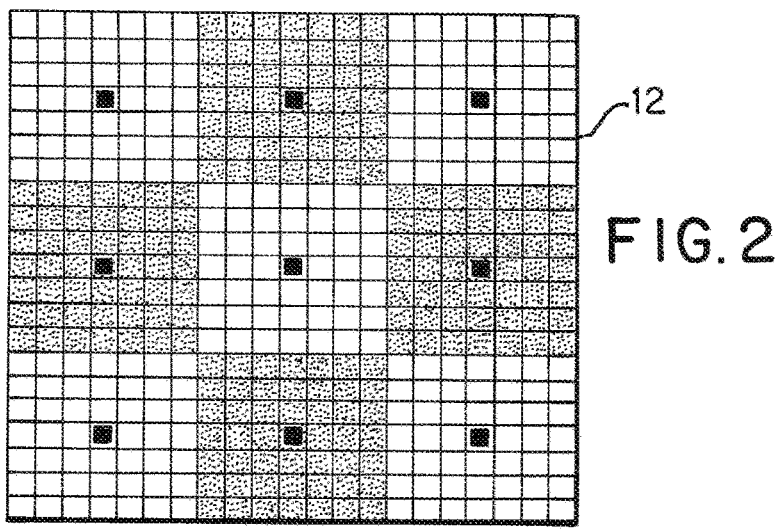
FIG. 2
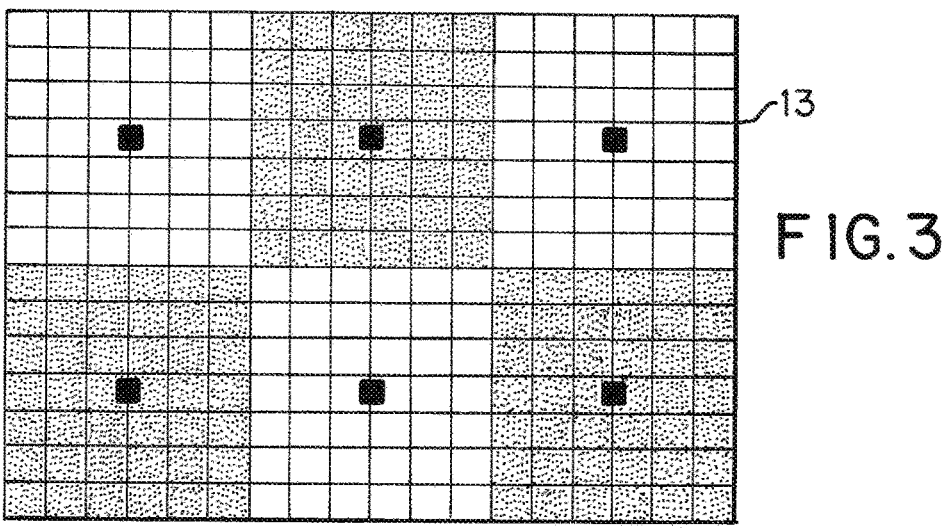
FIG. 3
FIG. 4A
VIEW A-A
FIG. 4B
FIG. 4C
DETAIL A
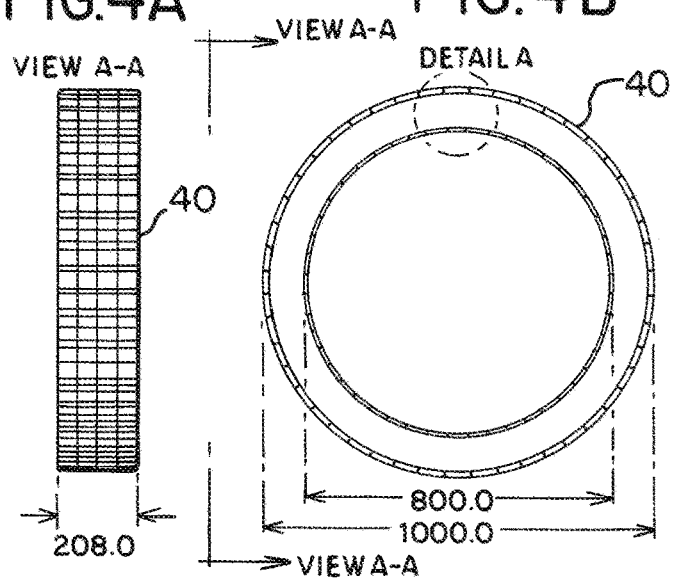
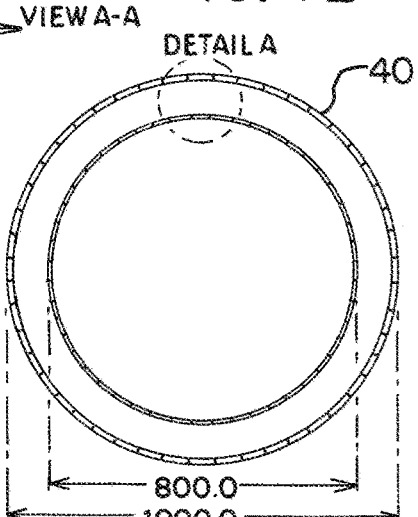
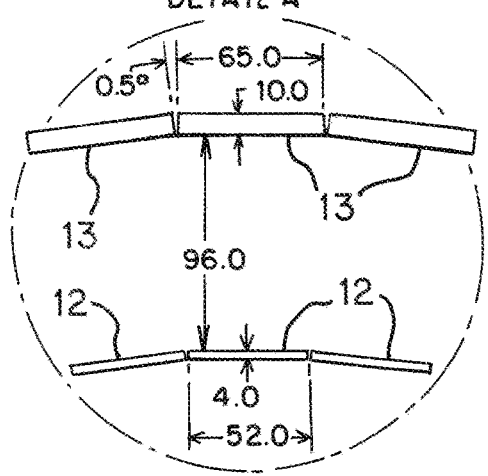

ADAPTIVE COMPTON CAMERA FOR MEDICAL IMAGING

BACKGROUND

The present embodiments relate to medical imaging using the Compton effect. The Compton effect allows for imaging higher energies than used for single photon emission computed tomography (SPECT). Compton imaging systems are constructed as test platforms, such as assembling a scatter layer and then a catcher layer mounted to a large framework. Electronics are connected to detect Compton-based events from emissions of a phantom. Compton imaging systems have failed to address design and constraint requirements for practical use in any commercial clinical settings. Current proposals lack the ability to be integrated into imaging platforms in the clinic or lack the design and constraint requirements (i.e., flexibility and scalability) to address commercial and diagnostic needs.

Compton-cameras may have low sensitivity ($) and poor image quality (IQ). The absolute number of scattered photons in the scatter layer is low due to the geometry (e.g., source-scatter solid angle $\Omega \ll 4\pi$), material (e.g., low scatter fraction in the detection material which favors photoelectric effect), and detector fabrication limitations (e.g., practical detector thickness that can be manufactured for both scatter and catcher layers is bounded, such as a maximum of ~1 mm for Si detectors and 2 mm . . . 10 mm for CZT detectors). The number of caught scattered photons in the catcher layer is low due to geometry (e.g., scatter-catcher solid angle $\Omega \ll 4\pi$). Doppler broadening degrades image quality of Compton cameras. The contribution of Doppler broadening to the Compton angle uncertainty depends on incident photon energy $E_0$, scattered angle $\theta$, and the energy of moving electrons bound to the target atom. Limited detector energy resolution causes additional Compton angle uncertainties. Limited detector position resolution in both scatter and catcher layers causes additional Compton cone annular offsets.

SUMMARY

By way of introduction, the preferred embodiments described below include methods and systems for medical imaging. To optimize image quality and/or sensitivity, the Compton camera is adaptable. The scatter and/or catcher detectors may move closer to and/or further away from a patient and/or each other. This adaptation allows a balancing of image quality and sensitivity by altering the geometry.

In a first aspect, a Compton camera is provided for medical imaging. A motor connects with a scatter detector, catcher detector, or both the scatter detector and the catcher detector. The motor is configured to move the scatter detector, catcher detector, or both the scatter detector and the catcher detector closer or further from the patient bed.

In a second aspect, a medical imaging system is provided. Solid-state detector modules each having a scatter detector and a catcher detector. A control processor is configured to alter a position of the scatter detector, the catcher detector, or both the scatter detector and the catcher detector relative to an isocenter of a patient space.

In a third aspect, a method is provided for medical imaging with a Compton camera. A motor moves a detector of the Compton camera. The detector as moved detects emissions from a patient. A Compton image is generated from the detected emissions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 2 illustrates an example scatter detector;

FIG. 3 illustrates an example catcher detector;

FIG. 4A is a side view of one embodiment of a Compton camera, FIG. 4B is an end view of the Compton camera of FIG. 4A, and FIG. 4C is a detail view of a part of the Compton camera of FIG. 4B;

DETAILED DESCRIPTION OF THE DRAWINGS AND PRESENTLY PREFERRED EMBODIMENTS

Figure 1:
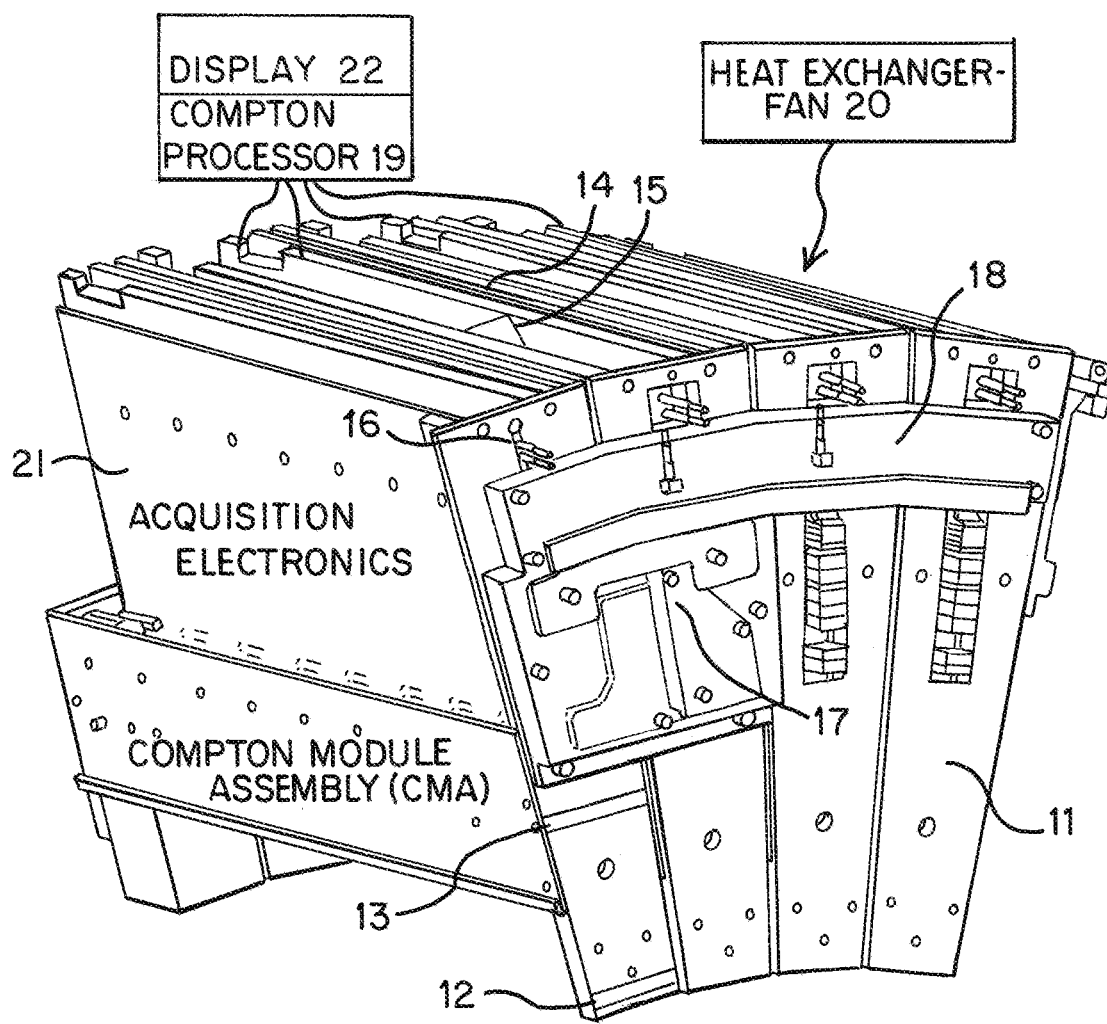
FIG. 1 is perspective view of multiple modules of a Compton camera according to one embodiment.

FIGS. 1-10 are directed to a multi-modality compatible Compton camera. A modular design is used to form the Compton camera for use with various other imaging modalities or as a stand-alone Compton-based medical imager. FIGS. 11-18 are directed to an adaptive Compton camera. Using the modular design of FIGS. 1-10 or another Compton camera (e.g., not modular), one or both scatter and detector layers are moveable relative to the patient for controlling the image quality, sensitivity, and/or other characteristic for improved diagnosis. After a summary of the adaptive Compton camera embodiments, the Compton camera of FIGS. 1-9 is described. Many of the features and components of the Compton camera of FIGS. 1-9 may be used in the adaptive Compton camera embodiments later described in FIGS. 11-18.

For the adaptive Compton-camera, the scatter and/or the catcher layer are moveable towards and away from the imaging object. The scatter layer may be positioned as close as possible to the imaging object, while the catcher layer for image quality may be positioned as far away as possible from the scatter layer. Both considerations may be used together within an 'adaptive' Compton-camera. By sensing the imaging object boundaries, the configuration of the Compton camera is changed. For example, the distance of each scatter layer to the imaging object and the distance of each catcher layer to each corresponding scatter layer are changed to maximize a given figure-of-merit (FOM). The FOM may be the sensitivity ($), image quality (IQ), and/or other parameters defined by the user. The sensitivity ($) may be improved by moving the scatter layer closer to the imaging object while image quality (IQ) may be improved by moving the catcher layer away from the imaging object. Moving the catcher layer closer to the scatter layer may improve the sensitivity, so the movement is based on the desired FOM for diagnostic purposes. A digital collimator may be used to filter out Compton scatter events that have a Compton angle above a threshold to deal with some uncertainty.

Referring to FIGS. 1-9, a medical imaging system includes a multi-modality compatible Compton camera with segmented detection modules. The Compton camera, such as a Compton camera ring, is segmented into modules that house the detection units. Each module is independent, and when assembled into a ring or partial ring, the modules may communicate with each other. The modules are independent yet can be assembled into a multi-module unit that produces Compton scattering-based images. Cylindrically symmetric modules or spherical shell segmented modules may be used.

The scatter-catcher pair, modular arrangement allows efficient manufacturing, is serviceable in the field, and is cost and energy efficient. The modules allow for the design freedom to change the radius for each radial detection unit, angular span of one module, and/or axial span. The scatter-catcher pair modules are multi-modality compatible and/or form a modular ring Compton camera for clinical emission imaging. This design allows flexibility, so the Compton camera may be added to existing computed tomography (CT), magnetic resonance (MR), positron emission tomography (PET) or other medical imaging platforms, either as axially separated systems or as fully integrated systems. Each module may address heat dissipation, data collection, calibration, and/or allow for efficient assembly as well as servicing.

Each scatter-catcher paired module is formed from commercially suitable solid-state detector modules (e.g., Si, CZT, CdTe, HPGe or similar), allowing for an energy range of 100-3000 keV. Compton imaging may be provided with a wider range of isotope energies (>2 MeV), enabling new tracers/markers through selection of the scatter-catcher detectors. The modularity allows for individual module removal or replacement, allowing for time and cost-efficient service. The modules may be operated independently and isolated or may be linked for cross-talk, allowing for improved image quality and higher efficiency in detecting Compton events using a scatter detector of one module and a catcher detector of another module.

The modularity allows for flexible design geometry optimized to individual requirements, such as using a partial ring for integration with a CT system (e.g., connected between the x-ray source and detector), a few modules (e.g., tiling) used for integration with a single photon emission computed tomography gamma camera or other space limited imaging system, or a full ring. Functional imaging based on Compton-detected events may be added to other imaging systems (e.g., CT, MR, or PET). Multiple full or partial rings may be placed adjacent to each other for greater axial coverage of the Compton camera. A dedicated or stand-alone Compton-based imaging system may be formed. In one embodiment, the modules include a collimator for lower energies (e.g., <300 keV), providing for multichannel and multiplexed imaging (e.g., high energies using the scatter-catcher detectors for Compton events and low energies using one of the detectors for SPECT or PET imaging). The modules may be stationary or fast rotating ($0.1 \text{ rpm} \ll \omega \ll 240 \text{ rpm}$). The dimensional, installation, service, and/or cost constraints are addressed by the scatter-catcher paired modules.

FIG. 1 shows one embodiment of modules 11 for a Compton camera. Four modules 11 are shown, but additional or fewer modules may be used. The Compton camera is formed from one or more modules, depending on the desired design of the Compton camera.

The Compton camera is for medical imaging. A space for a patient relative to the modules is provided so that the modules are positioned to detect photons emitted from the patient. A radiopharmaceutical in the patient includes a radio-isotope. A photon is emitted from the patient due to decay from the radio-isotope. The energy from the radio-isotope may be 100-3000 keV, depending on the material and structure of the detectors. Any of various radio-isotopes may be used for imaging a patient.

Each of the modules 11 includes the same or many of the same components. A scatter detector 12, a catcher detector 13, circuit boards 14, and baffle 15 are provided in a same housing 21. Additional, different, or fewer components may be provided. For example, the scatter detector 12 and catcher detector 13 are provided in the housing 21 without other components. As another example, a fiber optic data line 16 is provided in all or a sub-set of the modules 11.

The modules 11 are shaped for being stacked together. The modules 11 mate with each other, such as having matching indentation and extensions, latches, tongue-and-grooves, or clips. In other embodiments, flat or other surfaces are provided for resting against each other or a divider. Latches, clips, bolts, tongue-and-groove or other attachment mechanisms for attaching a module 11 to any adjacent modules 11 are provided. In other embodiments, the module 11 attaches to a gantry or other framework with or without direct connection to any adjacent modules 11.

The connection or connections to the other modules 11 or gantry may be releasable. The module 11 is connected and may be disconnected. The connection may be releasable, allowing removal of one module 11 or a group of modules 11 without removing all modules 11.

For forming a Compton camera from more than one module 11, the housing 21 and/or outer shape of the modules 11 is wedge shaped. The modules 11 may be stacked around an axis to form a ring or partial ring due to the wedge shape. The part closer to the axis has a width size that is narrower along a dimension perpendicular to the axis than a width size of a part further from the axis. In the modules 11 of FIG. 1, the housings 21 have the widest part furthest from the axis. In other embodiments, the widest part is closer to the axis but spaced away from the narrowest part closest to the axis.

In the wedge shape, the scatter detector 12 is nearer to the narrower part of the wedge shape than the catcher detector 13. This wedge shape in cross-section along a plane normal to the axis allows stacking of the modules 11 in abutting positions, adjacently, and/or connected to form at least part of a ring about the axis.

The taper of the wedge provides for a number N of modules 11 to form a complete ring around the axis. Any number N may be used, such as N=10-30 modules. The number N may be configurable, such as using different housings 21 for different numbers N. The number of modules 11 used for a given Compton camera may vary, depending on the design of the Compton camera (e.g., partial ring). The wedge shape may be provided along other dimensions, such as having a wedge shape in a cross-section parallel to the axis.

The modules 11 as stacked are cylindrically symmetric as connected with a gantry of a medical imaging system. A narrowest end of the wedged cross-section is closest to a patient space of the medical imaging system and a widest end of the wedged cross-section may be furthest from the patient space. In alternative embodiments, other shapes than wedge allowing for stacking together to provide a ring or generally curved shape of the stack may be provided.

The housing 21 is metal, plastic, fiberglass, carbon (e.g., carbon fiber), and/or other material. In one embodiment, different parts of the housing 21 are of different materials. For example, tin is used for the housing around the circuit boards 14. Aluminum is used to hold the scatter detector 12 and/or catcher detector 13. In another example, the housing 12 is of the same material, such as aluminum.

The housing 21 may be formed from different structures, such as end plates having the wedge shape, sheets of ground plane housing the circuit boards 14, and separate structure for walls holding the scatter detector 12 and catcher detector 13 where the separate structure is formed of material through which photons of a desired energy from a Compton event may pass (e.g., aluminum or carbon fiber). In alternative embodiments, walls are not provided for the modules 11 between the end plates for a region where the scatter detector 12 and/or catcher detector 13 are positioned, avoiding interference of photons passing from the scatter detector 12 of one module 11 to a catcher detector 13 of another module 11. The housing 21 by and/or for holding the detectors 12, 13 is made of low attenuating material, such as aluminum or carbon fiber.

The housing 21 may seal the module or includes openings. For example, openings for air flow are provided, such as at a top of widest portion of the wedge shape at the circuit boards 14. The housing 21 may include holes, grooves, tongues, latches, clips, stand-offs, bumpers, or other structures for mounting, mating, and/or stacking.

Each of the solid-state detector modules 11 includes both scatter and catcher detectors 12, 13 of a Compton sensor. By stacking each module, the size of the Compton sensor is increased. A given module 11 itself may be a Compton sensor since both the scatter detector 12 and catcher detector 13 are included in the module 11.

The modules 11 may be separately removed and/or added to the Compton sensor. For a given module 11, the scatter detector 12 and/or catcher detector 13 may be removable from the module 11. For example, a module 11 is removed for service. A faulty one or both detectors 12, 13 are removed from the module 11 for replacement. Once replaced, the refurbished module 11 is placed back in the medical imaging system. Bolts, clips, latches, tongue-and-groove, or other releasable connectors may connect the detectors 12, 13 or part of the housing 21 for the detectors 12, 13 to the rest of the module 11.

The scatter detector 12 is a solid-state detector. Any material may be used, such as Si, CZT, CdTe, HPGe, and/or other material. The scatter detector 12 is created with wafer fabrication at any thickness, such as about 4 mm for CZT. Any size may be used, such as about 5×5 cm. FIG. 2 shows a square shape for the scatter detector 12. Other shapes than square may be used, such as rectangular. For the modules 11 of FIG. 1, the scatter detector 12 may be rectangular extending between two wedge-shaped end-plates.

In the module 11, the scatter detector 12 has any extent. For example, the scatter detector 12 extends from one wedge-shaped end wall to the other wedge-shaped end wall. Lesser or greater extent may be provided, such as extending between mountings within the module 11 or extending axially beyond one or both end-walls. In one embodiment, the scatter detector 12 is at, on, or by one end wall without extended to another end wall.

The scatter detector 12 forms an array of sensors. For example, the 5×5 cm scatter detector 12 of FIG. 2 is a 21×21 pixel array with a pixel pitch of about 2.2 mm. Other numbers of pixels, pixel pitch, and/or size of arrays may be used.

The scatter detector 12 includes semiconductor formatted for processing. For example, the scatter detector 12 includes an application specific integrated circuit (ASIC) for sensing photon interaction with an electron in the scatter detector 12. The ASIC is collocated with the pixels of the scatter detector 12. The ASIC is of any thickness. A plurality of ASICs may be provided, such as 9 ASICS in a 3×3 grid of the scatter detector 12.

The scatter detector 12 may operate at any count rate, such as >100 kcps/mm. Electricity is generated by a pixel due to the interaction. This electricity is sensed by the application specific integrated circuit. The location, time, and/or energy is sensed. The sensed signal may be conditioned, such as amplified, and sent to one or more of the circuit boards 14. A flexible circuit, wires, or other communications path carries the signals from the ASIC to the circuit board 14.

Compton sensing operates without collimation. Instead, a fixed relationship between energy, position, and angle of a photon interaction at the scatter detector 12 relative to a photon interaction at the catcher detector 13 is used to determine the angle of the photon entering the scatter detector 12. A Compton process is applied using the scatter detector 12 and the catcher detector 13.

The catcher detector 13 is a solid-state detector. Any material may be used, such as Si, CZT, CdTe, HPGe, and/or other material. The catcher detector 13 is created with wafer fabrication at any thickness, such as about 10 mm for CZT. Any size may be used, such as about 5×5 cm. The size may be larger along at least one dimension than the scatter detector 12 due to the wedge shape and spaced apart positions of the scatter detector 12 and the catcher detector 13. FIG. 3 shows a rectangular shape for the catcher detector 13 but other shapes may be used. For the modules 11 of FIG. 1, the catcher detector 13 may be rectangular extending between two end-plates where the length is the same as and the width is greater than the scatter detector 12.

The catcher detector 12 forms an array of sensors. For example, the 5×6 cm catcher detector 13 of FIG. 3 is a 14×18 pixel array with a pixel pitch of about 3.4 mm. The pixel size is larger than the pixel size of the scatter detector 12. The number of pixels is less than the number of pixels of the scatter detector 12. Other numbers of pixels, pixel pitch, and/or size of arrays may be used. Other relative pixels sizes and/or numbers of pixels may be used.

In the module 11, the catcher detector 13 has any extent. For example, the catcher detector 13 extends from one wedge-shaped end wall to the other wedge-shaped end wall. Lesser or greater extent may be provided, such as extending between mountings within the module 11 or extending axially beyond one or both end-walls. In one embodiment, the catcher detector 13 is at, on, or by one end wall without extending to another end wall.

The catcher detector 13 includes semiconductor formatted for processing. For example, the catcher detector 13 includes an ASIC for sensing photon interaction with an electron in the catcher detector 13. The ASIC is collocated with the pixels of the catcher detector 13. The ASIC is of any thickness. A plurality of ASICS may be provided, such as 6 ASICS in a 2×3 grid of the catcher detector 13.

The catcher detector 13 may operate at any count rate, such as >100 kcps/mm. Electricity is generated by a pixel due to the interaction. This electricity is sensed by the ASIC. The location, time, and/or energy is sensed. The sensed signal may be conditioned, such as amplified, and sent to one or more of the circuit boards 14. A flexible circuit, wires, or other communications path carries the signals from the ASIC to the circuit board 14.

The catcher detector 13 is spaced from the scatter detector 12 by any distance along a radial line from the axis or normal to the parallel scatter and catcher detectors 12, 13. In one embodiment, the separation is about 20 cm, but greater or lesser separation may be provided. The space between the catcher detector 13 and the scatter detector 12 is filled with air, other gas, and/or other material with low attenuation for photons at the desired energies.

The circuit boards 14 are printed circuit boards, but flexible circuits or other materials may be used. Any number of circuit boards 14 for each module may be used. For example, one circuit board 14 is provided for the scatter detector 12 and another circuit board 14 is provided for the catcher detector 13.

The circuit boards 14 are within the housing 21 but may extend beyond the housing 21. The housing 21 may be grounded, acting as a ground plane for the circuit boards 14. The circuit boards 14 are mounted in parallel with each other or are non-parallel, such as spreading apart in accordance with the wedge shape. The circuit boards are positioned generally orthogonal to the catcher detector 13. Generally is used to account for any spread due to the wedge shape. Brackets, bolts, screws, and/or stand-offs from each other and/or the housing 21 are used to hold the circuit boards 14 in place.

The circuit boards 14 connect to the ASICS of the scatter and catcher detectors 12, 13 through flexible circuits or wires. The ASICs output detected signals. The circuit boards 14 are acquisition electronics, which process the detected signals to provide parameters to the Compton processor 19. Any parameterization of the detected signals may be used. In one embodiment, the energy, arrival time, and position in three-dimensions is output. Other acquisition processing may be provided.

The circuit boards 14 output to each other, such as through a galvanic connection within a module 11, to the data bridge 17, and/or to a fiber optic data link 16. The fiber data link 16 is a fiber optic interface for converting electrical signals to optical signals. A fiber optic cable or cables provide the acquisition parameters for events detected by the scatter and catcher detectors 12, 13 to the Compton processor 19.

The data bridge 17 is a circuit board, wires, flexible circuit, and/or other material for galvanic connection to allow communications between modules 11. A housing or protective plate may cover the data bridge 17. The data bridge 17 releasably connects to one or more modules 11. For example, plugs or mated connectors of the data bridge 17 mate with corresponding plugs or mated connectors on the housing 21 and/or circuit boards 14. A latch, clip, tongue-and-groove, screw, and/or bolt connection may be used to releasably hold the data bridge 17 in place with the modules 11.

The data bridge 17 allows communications between the modules. For example, the fiber data link 16 is provided in one modules 11 and not another module 11. The cost of a fiber data link 16 in every module 11 is avoided. Instead, the parameters output by the other module 11 are provided via the data bridge 17 to the module 11 with the fiber data link 16. The circuit board or boards 14 of the module 11 with the fiber data link 16 route the parameter output to the fiber data link 16, using the fiber data link 16 to report detected events from more than one module 11. In alternative embodiments, each module 11 includes a fiber data link 16, so the data bridge 17 is not provided or communicates other information.

The data bridge 17 may connect other signals between the modules 11. For example, the data bridge 17 includes a conductor for power. Alternatively, a different bridge provides power to the modules 11 or the modules 11 are individually powered. As another example, clock and/or synchronization signals are communicated between modules 11 using the data bridge 17.

In the embodiment of FIG. 1, a separate clock and/or synchronization bridge 18 is provided. The clock and/or synchronization bridge 18 is a circuit board, wires, flexible circuit, and/or other material for galvanic connection to allow communication of clock and/or synchronization signals between modules 11. A housing or protective plate may cover the clock and/or synchronization bridge 18. The clock and/or synchronization bridge 18 releasably connects to one or more modules 11. For example, plugs or mated connectors of the clock and/or synchronization bridge 18 mate with corresponding plugs or mated connectors on the housing 21 and/or circuit boards 14. A latch, clip, tongue-and-groove, screw, and/or bolt connection may be used to releasably hold the clock and/or synchronization bridge 18 in place with the modules 11.

The clock and/or synchronization bridge 18 may connect with the same or different grouping of modules 11 as the data bridge 17. In the embodiment shown in FIG. 1, the data bridge 17 connects between pairs of modules 11 and the clock and/or synchronization bridge 18 connects over groups of four modules 11.

The clock and/or synchronization bridge 18 provides a common clock signal and/or synchronization signals for synchronizing clocks of the modules 11. One of the parameters formed by the circuit boards 14 of each module 11 is the time of detection of the event. Compton detection relies on pairs of events—a scatter event and a catcher event. Timing is used to pair events from the different detectors 12, 13. The common clocking and/or synchronization allows for accurate pairing where the pair of events are detected in different modules 11. In alternative embodiments, only scatter and catcher events detected in a same module 11 are used, so the clock and/or synchronization bridge 18 may not be provided.

Other links or bridges between different modules 11 may be provided. Since the bridges 17, 18 are removable, individual modules 11 may be removed for service while leaving remaining modules 11 in the gantry.

Each module 11 is air cooled. Holes may be provided for forcing air through the module 11 (i.e., entry and exit holes). One or more baffles 15 may be provided to guide the air within the module 11. Water, conductive transfer, and/or other cooling may be alternatively or additionally provided.

In one embodiment, the top portion of the wedge-shape module 11 or housing 21 is open (i.e., no cover on the side furthest from the patient area). One or more baffles 15 are provided along the centers of one or more circuit boards 14 and/or the housing 21. A fan and heat exchanger 20 force cooled or ambient temperature air into each module 11, such as along one half of the module 11 at a location spaced away from the catcher detector 13 (e.g., top of the module 11). The baffles 15 and/or circuit boards 14 guide at least some of the air to the airspace between the scatter detector 12 and the catcher detector 13. The air then passes by the baffles 15 and/or circuit boards 14 on another part (e.g., another half) of the module 11 for exiting to the heat exchanger 20. Other routing of the air may be provided.

The heat exchanger and fan 20 is provided for each individual module 11, so may be entirely or partly within the module 11. In other embodiments, ducting, baffles, or other structure route air to multiple modules 11. For example, groups of four modules 11 share a common heat exchanger and fan 20, which is mounted to the gantry or other framework for cooling the group of modules 11.

For forming a Compton sensor, one or more modules 11 are used. For example, two or more modules 11 are positioned relative to a patient bed or imaging space to detect photon emissions from the patient. An arrangement of a greater number of modules 11 may allow for detection of a greater number of emissions. By using the wedge shape, modules 11 may be positioned against, adjacent, and/or connected with each other to form an arc about the patient space. The arc may have any extent. The modules 11 directly contact each other or contact through spacers or the gantry with small separation (e.g., 10 cm or less) between the modules 11.

In one example, four modules 11 are positioned together, sharing a clock and/or synchronization bridge 18, one or more data bridges 17, and a heat exchanger and fan 20. One, two, or four fiber data links 16 are provided for the group of modules 11. Multiple such groups of modules 11 may be positioned apart or adjacent to each other for a same patient space.

Due to the modular approach, any number of modules 11 may be used. Manufacturing is more efficient and costly by building multiple of the same component despite use of any given module 11 in a different arrangement than used for others of the modules 11.

The fiber data links 16 of the modules 11 or groups of modules 11 connect to the Compton processor 19. The Compton processor 19 receives the values for the parameters for the different events. Using the energy and timing parameters, scatter and catcher events are paired. For each pair, the spatial locations and energies of the pair of events are used to find the angle of incidence of the photon on the scatter detector 12. The event pairs are limited to events in the same module 11 in one embodiment. In another embodiment, catcher events from the same or different modules 11 may be paired with scatter events from a given module 11. More than one Compton processor 19 may be used, such as for pairing events from different parts of a partial ring 40.

Once paired events are linked, the Compton processor 19 or another processor may perform computed tomography to reconstruct a distribution in two or three dimensions of the detected emissions. The angle or line of incidence for each event is used in the reconstruction. The reconstructed distribution of emissions is used to generate a Compton image.

The display 22 is a CRT, LCD, projector, printer, or other display. The display 22 is configured to display the Compton image. The image or images are stored in a display plane buffer and read out to the display 22. The images may be displayed separately or are combined, such as displaying the Compton image overlaid with or adjacent to a SPECT image.

Figure 5:
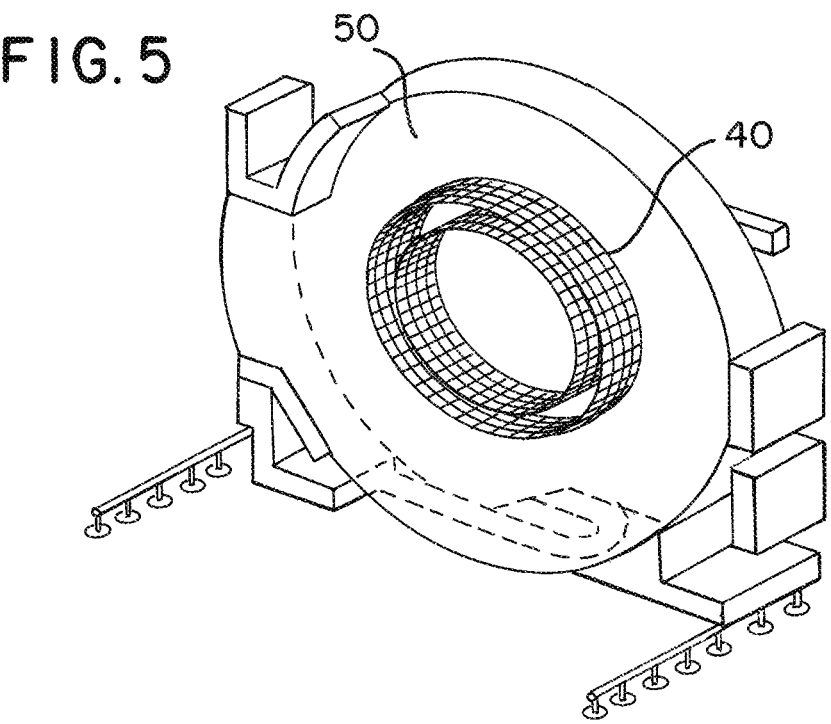
FIG. 5 is a perspective view of one embodiment of a Compton camera in a medical imaging system.
Figure 6:
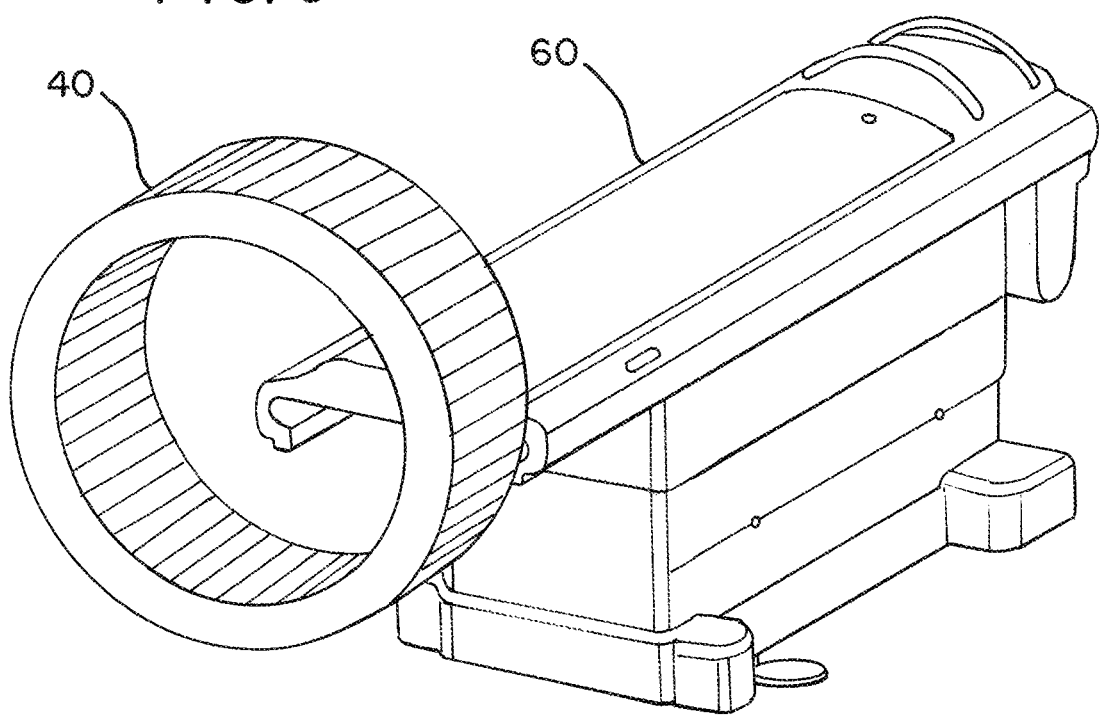
FIG. 6 is a perspective view of one embodiment of a full-ring Compton camera in a medical imaging system.

FIGS. 4A-6 shows one example arrangement of modules 11. The modules 11 form a ring 40 surrounding a patient space. FIG. 4A shows four such rings 40 stacked axially. FIG. 4B shows the scatter detectors 12 and corresponding catcher detectors 13 of the modules 11 in the ring 40. FIG. 4C shows a detail of a part of the ring 40. Three modules 11 provide corresponding pairs of scatter and catcher detectors 12, 13. Other dimensions than shown may be used. Any number of modules 11 may be used to form the ring 40. The ring 40 completely surrounds the patient space. Within a housing of a medical imaging system, the ring 40 connects with a gantry 50 or another framework as shown in FIG. 5. The ring 40 may be positioned to allow a patient bed 60 to move a patient into and/or through the ring 40. FIG. 6 shows an example of this configuration.

Figure 7:
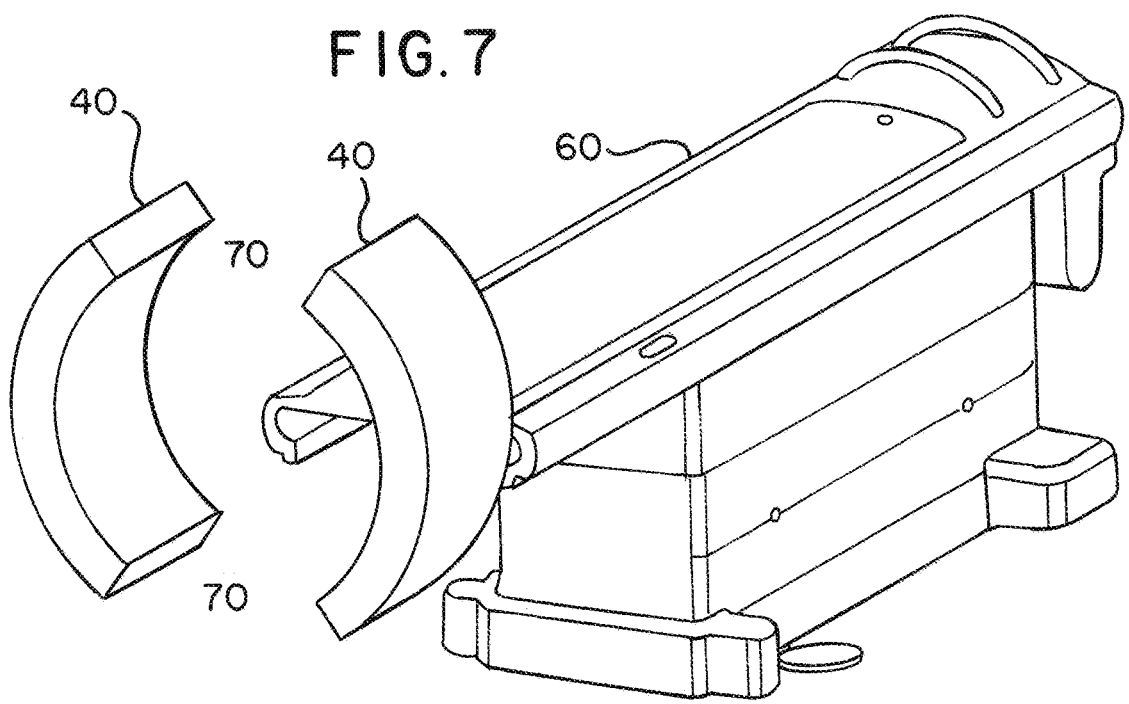
FIG. 7 is a perspective view of one embodiment of a partial-ring Compton camera in a medical imaging system.

The ring may be used for Compton-based imaging of emissions from a patient. FIG. 7 shows an example of using the same type of modules 11 but in a different configuration. A partial ring 40 is formed. One or more gaps 70 are provided in the ring 40. This may allow for other components to be used in the gaps and/or to make a less costly system by using fewer modules 11.

Figure 8:
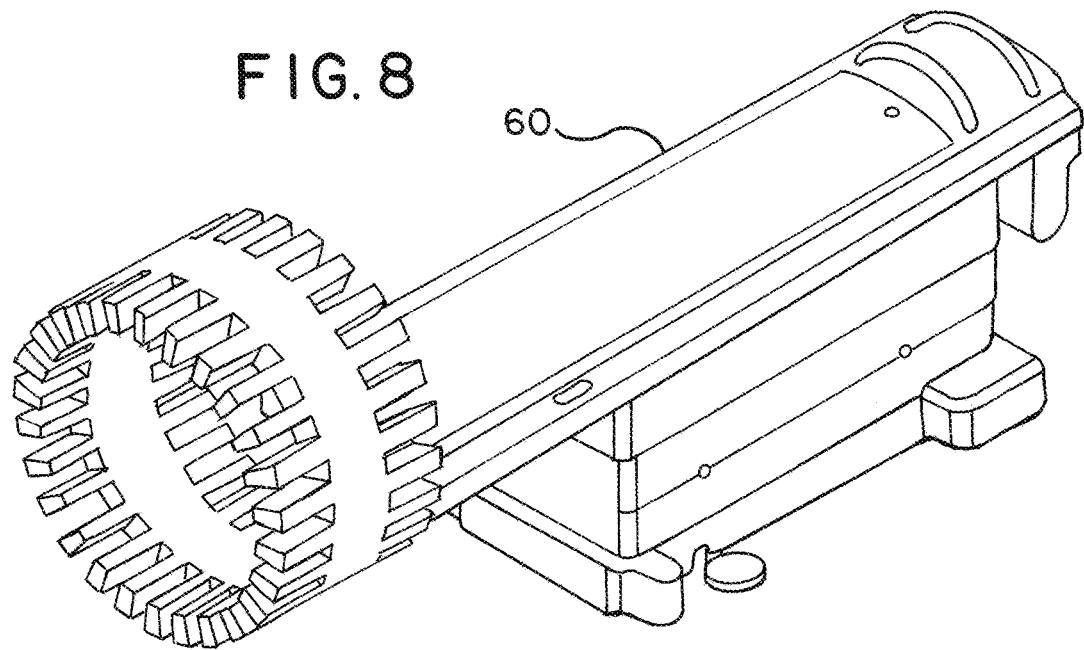
FIG. 8 is a perspective view of one embodiment of a full-ring Compton camera with partial-rings in axial extension in a medical imaging system.

FIG. 8 shows another configuration of modules 11. The ring 40 is a full ring. Additional partial rings 80 are stacked axially relative to the bed 60 or patient space, extending the axial extent of detected emissions. The partial rings 80 are in an every other or every group of N modules 11 (e.g., N=4) distribution rather than the two gaps 70 partial ring 40 of FIG. 7. The additional rings may be full rings. The full ring 40 may be a partial ring 80. The different rings 40 and/or partial rings 80 are stacked axially with no or little (e.g., less than ½ a module's 11 axial extent) apart. Wider spacing may be provided, such as having a gap of more than one module's 11 axial extent.

Figure 9:
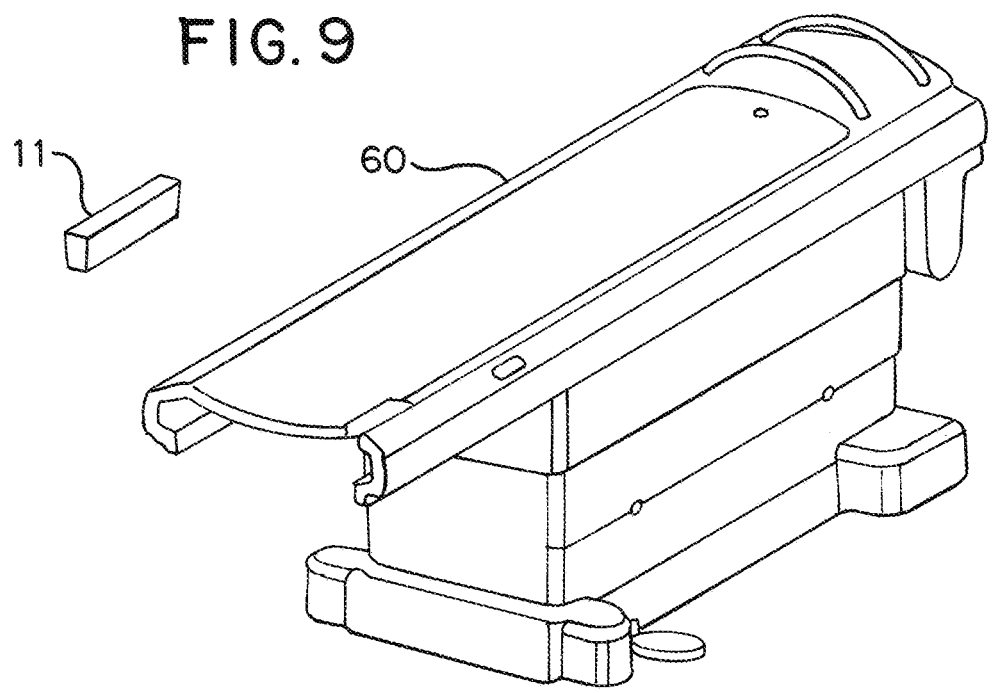
FIG. 9 is a perspective view of one embodiment of a single module-based Compton camera in a medical imaging system.

FIG. 9 shows yet another configuration of modules 11. One module 11 or a single group of modules 11 is positioned by the patient space or bed 60. Multiple spaced apart single modules 11 or groups (e.g., group of four) may be provided at different locations relative to the bed 60 and/or patient space.

In any of the configurations, the modules 11 are held in position by attachment to a gantry, gantries, and/or other framework. The hold is releasable, such as using bolts or screws. The desired number of modules 11 are used to assemble the desired configuration for a given medical imaging system. The gathered modules 11 are mounted in the medical imaging system, defining or relative to the patient space. The result is a Compton sensor for imaging the patient.

The bed 60 may move the patient to scan different parts of the patient at different times. Alternatively or additionally, the gantry 50 moves the modules 11 forming the Compton sensor. The gantry 50 translates axially along the patient space and/or rotates the Compton sensor around the patient space (i.e., rotating about the long axis of the bed 60 and/or patient). Other rotations and/or translations may be provided, such as rotating the modules 11 about an axis non-parallel to the long axis of the bed 60 or patient. Combinations of different translations and/or rotations may be provided.

The medical imaging system with the Compton sensor is used as a standalone imaging system. Compton sensing is used to measure distribution of radiopharmaceutical in the patient. For example, the full ring 40, partial ring 40, and/or axially stacked rings 40, 80 are used as a Compton-based imaging system.

In other embodiments, the medical imaging system is a multi-modality imaging system. The Compton sensor formed by the modules 11 is one modality, and another modality is also provided. For example, the other modality is a single photon emission computed tomography (SPECT), a PET, a CT, or a MR imaging system. The full ring 40, partial ring 40, axially stacked rings 40,80, and/or singular module 11 or group of modules 11 are combined with the sensors for the other type of medical imaging. The Compton sensor may share a bed 60 with the other modality, such as being positioned along a long axis of the bed 60 where the bed positions the patient in the Compton sensor in one direction and in the other modality in the other direction.

The Compton sensor may share an outer housing with the other modality. For example, the full ring 40, partial ring 40, axially stacked rings 40,80, and/or singular module 11 or group of modules 11 are arranged within a same imaging system housing for the sensor or sensors of the other modality. The bed 60 positions the patient within the imaging system housing relative to the desired sensor. The Compton sensor may be positioned adjacent to the other sensors axially and/or in a gap at a same axial location. In one embodiment, the partial ring 40 is used in a computed tomography system. The gantry holding the x-ray source and the x-ray detector also holds the modules 11 of the partial ring 40. The x-ray source is in one gap 70, and the detector is in another gap 70. In another embodiment, the single module 11 or a sparse distribution of modules 11 connects with a gantry of a SPECT system. The module 11 is placed adjacent to the gamma camera, so the gantry of the gamma camera moves the module 11. Alternatively, a collimator may be positioned between the modules 11 and the patient or between the scatter and catcher detectors 12, 13, allowing the scatter and/or catcher detectors 12, 13 of the modules 11 to be used for photoelectric event detection for SPECT imaging instead of or in addition to detection of Compton events.

The module-based segmentation of the Compton sensor allows the same design of modules 11 to be used in any different configurations. Thus, a different number of modules 11, module position, and/or configuration of modules 11 may be used for different medical imaging systems. For example, one arrangement is provided for use with one type of CT system and a different arrangement (e.g., number and/or position of modules 11) is used for a different type of CT system.

The module-based segmentation of the Compton sensor allows for more efficient and costly servicing. Rather than replacing an entire Compton sensor, any module 11 may be disconnected and fixed or replaced. The modules 11 are individually connectable and disconnectable from each other and/or the gantry 50. Any bridges are removed, and then the module 11 is removed from the medical imaging system while the other modules 11 remain. It is cheaper to replace an individual module 11. The amount of time to service may be reduced. Individual components of a defective module 11 may be easily replaced, such as replacing a scatter or catcher detector 12, 13 while leaving the other. The modules 11 may be configured for operation with different radioisotopes (i.e., different energies) by using corresponding detectors 12, 13.

Figure 10:
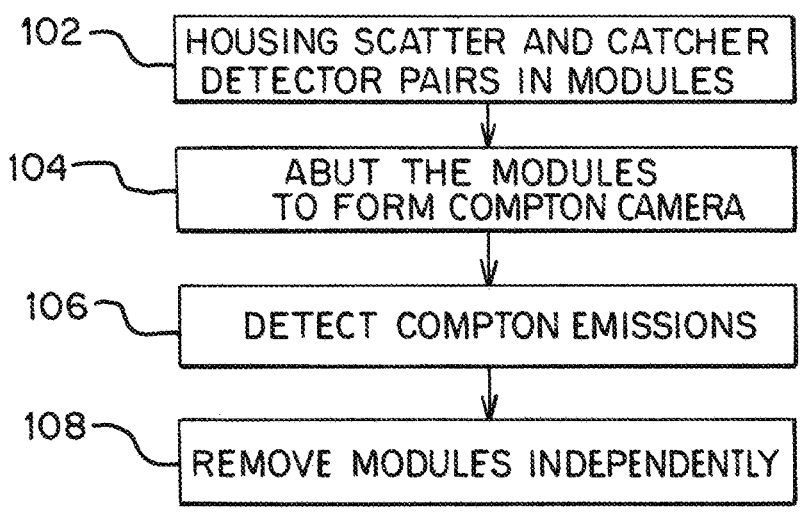
FIG. 10 is a flow chart diagram of an example embodiment of a method for forming a Compton camera.

FIG. 10 shows one embodiment of a flow chart of a method for forming, using, and repairing a Compton camera. The Compton camera is formed in a segmented approach. Rather than hand assembling the entire camera in place, scatter detector and catcher detector pairs are positioned relative to each other to form a desired configuration of the Compton camera. This segmented approach may allow different configurations using the same parts, ease of assembly, ease of repair, and/or integration with other imaging modalities.

Figure 11:
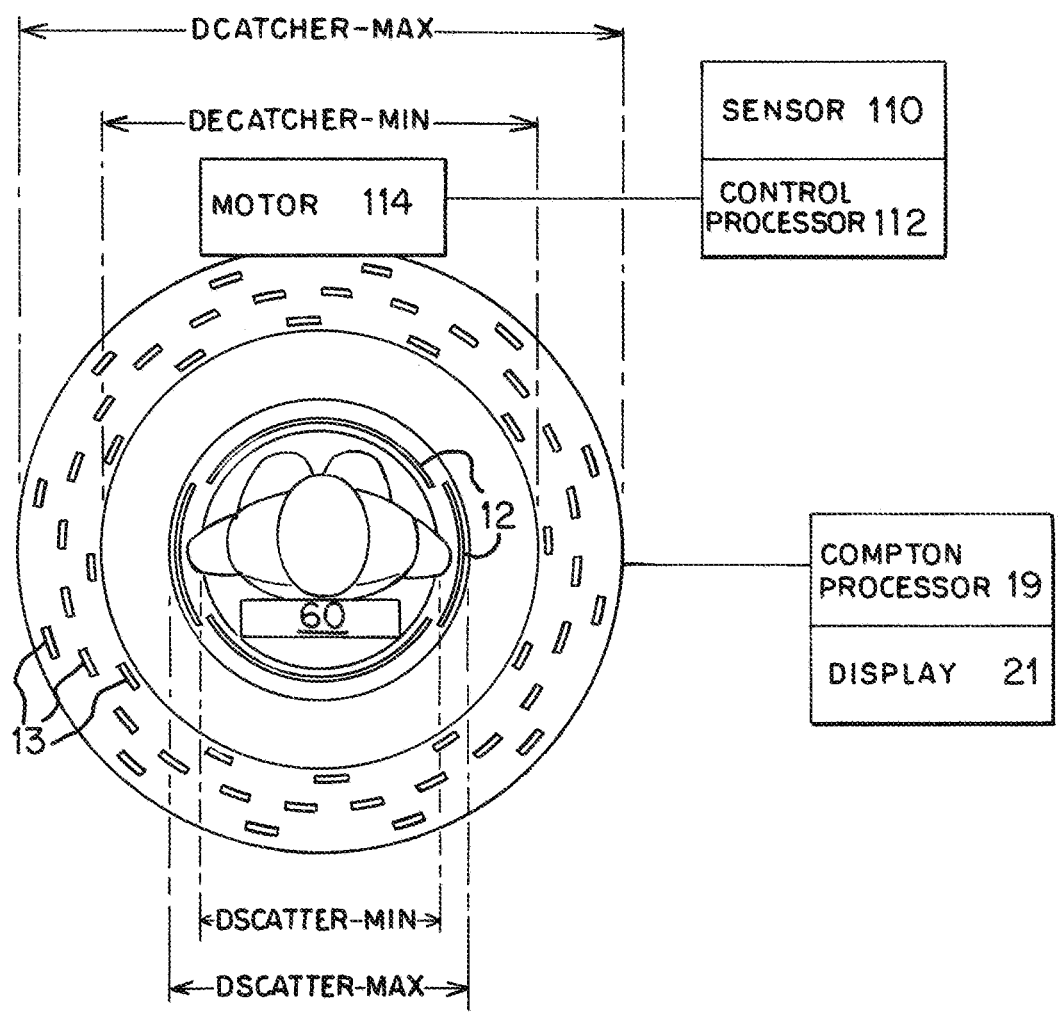
FIG. 11 is a cross-section view of one embodiment of an adaptive Compton camera for medical imaging.

Other embodiments form a combination of a Compton camera and a SPECT camera. The segmented modules 11 of FIG. 11 are used. The modules of FIGS. 13-16 may be used for forming a SPECT camera. The detector arrangement of FIG. 11 may be used.

The method may be implemented by the system of FIG. 1 to assemble a Compton sensor as shown in any of FIGS. 4-9. The method may be implemented by the system of FIG. 11 to assemble a Compton sensor as shown in any of FIGS. 13-16. Other systems, modules, and/or configured Compton sensors may be used.

The acts are performed in the order shown (i.e., top to bottom or numerically) or other orders. For example, act 108 may be performed as part of act 104.

Additional, different, or fewer acts may be provided. For example, acts 102 and 104 are provided for assembling the Compton camera without performing acts 106 and 108. As another example, act 106 is performed without other acts.

In act 102, scatter and catcher detector pairs are housed in separate housings. Modules are assembled where each module includes both a scatter detector and a catcher detector. A machine and/or person manufactures the housings.

The modules are shaped to abut where the scatter and catcher detector pairs of different ones of the housings are non-planar. For example, a wedge shape and/or positioning is provided so that the detector pairs from an arc, such as shown in FIG. 4C. The shape allows and/or forces the arc shape when the modules are positioned against one another.

In act 104, the housings are abutted. A person or machine assembles the Compton sensor from the housings. By stacking the housings adjacent to each other with direct contact or contact through spacers, gantry, or framework, the abutted housings form the arc. A full ring or partial ring is formed around and at least in part defines a patient space. Based on the design of the Compton camera or Compton-SPECT camera, any number of housings with the corresponding scatter and catcher detector pairs are positioned together to form a camera.

The housings may be abutted as part of a multi-modality system or to create a single imaging system. For a multi-modality system, the housings are positioned in a same outer housing and/or relative to a same bed as the sensors for the other modality, such as SPECT, PET, CT, or MR imaging system. The same or different gantry or support framework may be used for the housings of the Compton camera and the sensors for the other modality. For other embodiments, the modules provide the multi-modality by providing for both a Compton camera and the SPECT imaging system.

The configuration or design of the Compton camera defines the number and/or position of the housings. Once abutted, the housings may be connected for communications, such as through one or more bridges. The housings may be connected with other components, such as an air cooling system and/or a Compton processor.

In act 106, the assembled Compton camera detects emissions. A given emitted photon interacts with the scatter detector. The result is scattering of another photon at a particular angle from the line of incidence of the emitted photon. This secondary photon has a lesser energy. The secondary photon is detected by the catcher detector. Based on the energy and timing of both the detected scatter event and catcher event, the events are paired. The positions and energies for the paired events provides a line between the detectors and an angle of scattering. As a result, the line of incidence of the emitted photon is determined.

To increase the likelihood of detecting the secondary photon, the catcher events from one housing may be paired with the scatter events of another housing. Due to the angles, scatter from one scatter detector may be incident on the paired catcher detector in the same housing or a catcher detector in another housing. By the housings being open in the detector region and/or using low photon attenuating materials, a greater number of Compton events may be detected.

The detected events are counted or collected. The lines of response or lines along which the different Compton events occur are used in reconstruction. The distribution in three dimensions of the emissions from the patient may be reconstructed based on the Compton sensing. The reconstruction does not need a collimator as the Compton sensing accounts for or provides the angle in incidence of the emitted photon.

The detected events are used to reconstruct the locations of the radioisotope. Compton and/or photoelectric images are generated from the detected events and corresponding line information from the events.

In act 108, a person or machine (e.g., robot) removes one of the housings. When one of the detectors or associated electronics of a housing fails or is to be replaced for detecting at different energies, the housing may be removed. The other housings are left in the medical imaging system. This allows for easier repair and/or replacement of the housing and/or detectors without the cost of a greater disassembly and/or replacement of the entire Compton camera.

FIGS. 11-18 are directed to an adaptive Compton camera. Using the modules of FIGS. 1-9 or another Compton camera, the scatter and/or catcher layers have an adaptive geometry to optimize a figure of merit (FOM) for a given imaging situation (e.g., patient, type of examination, application, energy of radioisotope emission, size of lesion, type of lesion (e.g., hot or cold), activity concentration . . . ).

FIG. 11 shows one embodiment of a Compton camera for medical imaging. This medical imaging system includes a scatter layer that may have two or more configurations, such as different distances from the isocenter. This medical imaging system includes a catcher layer that may have two or more configurations, such as three different distances from the isocenter. By selecting the positions of the scatter and/or catcher layer, the adaptive configuration may be used to optimize or improve image quality (IQ) and/or sensitivity ($). The 'adaptive' scatter and/or catcher layers are positioned based on user requirements (e.g., FOM) and/or a contour of the imaged object.

The medical imaging system includes the scatter detectors 12, catcher detectors 13, patient bed 60, a sensor 110, a control processor 112, a motor 114, the Compton processor 19, and the display 22. Additional, different, or fewer components may be provided. For example, the sensor 110 is not provided. As another example, the Compton processor 19 and/or display 22 are not provided. The Compton processor 19 and the control processor 112 may be a same processor. In yet another example, a user interface (e.g., user input device) is provided for an operator selection of a FOM or input of a patient size.

The patient bed 60 supports the patient in a patient space. The bed 60 may be moveable, such as a robot or roller system for moving the patient into and out of the medical imaging system. The outer housing of the medical imaging system and/or scatter layer create a bore into which the patient bed 60 is positioned. The bore defines a patient space for imaging the patient. The bore may be of any dimension in a cross-sectional plane orthogonal to a longitudinal axis, such as 70 cm.

The scatter layer is formed from a plurality of scatter detectors 12, such as using the modular system of FIGS. 1-9. Similarly, the catcher layer 13 is formed from a plurality of catcher detectors 13. For example, forty-eight modules 11 provide for forty-eight pairs of scatter and catcher detectors 12, 13 shown in FIG. 11. More or fewer modules 11 may be used. The modules 11 have any arrangement, such as one or more axially spaced rings and/or partial rings or one or more sparsely distributed modules 11 or groups of modules. The modules 11 may be part of a multi-modality imaging system or for a Compton-camera only system. The scatter and catcher detectors 12, 13 (e.g., modules 11) are positioned to receive emissions from a patient on the patient bed 60 or otherwise in the patient space.

The sensor 110 is a depth camera, optical camera, infrared sensor, LIDAR, or other sensor for detecting a location of an outer surface of the patient in the patient space or on the bed 60. The sensor 110 communicatively connects with the control processor 112 for sending measurements or calculated distances to the control processor 112.

The sensor 110 may directly measure the position of the outer surface as a distance from the sensor 110 and/or may apply image processing to determine the position (e.g., processing an image of a projected grid). While one sensor 110 is shown, more than one sensor may be used to measure the patient position at an axial position (i.e., long axis of the bore or patient) of the detectors 12, 13. Different parts of the patient have different extents or distances away from the isocenter and/or the scatter detectors 12. In one embodiment, each module 11 includes a distance sensor 110 to measure a distance from the module 11 and/or scatter detector 12 of the patient at the location of the module 11. A single sensor 110 or fewer sensors 110 than modules 11 may be used where the sensor or sensors 110 determine the position of the surface of the patient at multiple locations on the patient.

The motor 114 is a servo, electric motor, hydraulic motor, pneumatic motor, or other motor for moving one or more of the detectors 12, 13. In one embodiment, one or more motors 114 are provided for each module 11 and/or for each detector 12, 13. The motor 114 electrically connects with the control processor 112 for control of operation of the motor 114 to move the detectors 12, 13. A position sensor, such as a sensor to determine the motor position and/or to determine a detector position, may be provided.

The motor 114 connects with the scatter detector 12, catcher detector 13, or both. The connection is through a chain, screw drive, rack and pinion (e.g., gearing) or other physical connection for translating motor movement (e.g., spinning of a shaft) to translation of the detector or detectors 12, 13 to or away from the patient space.

Figure 12:
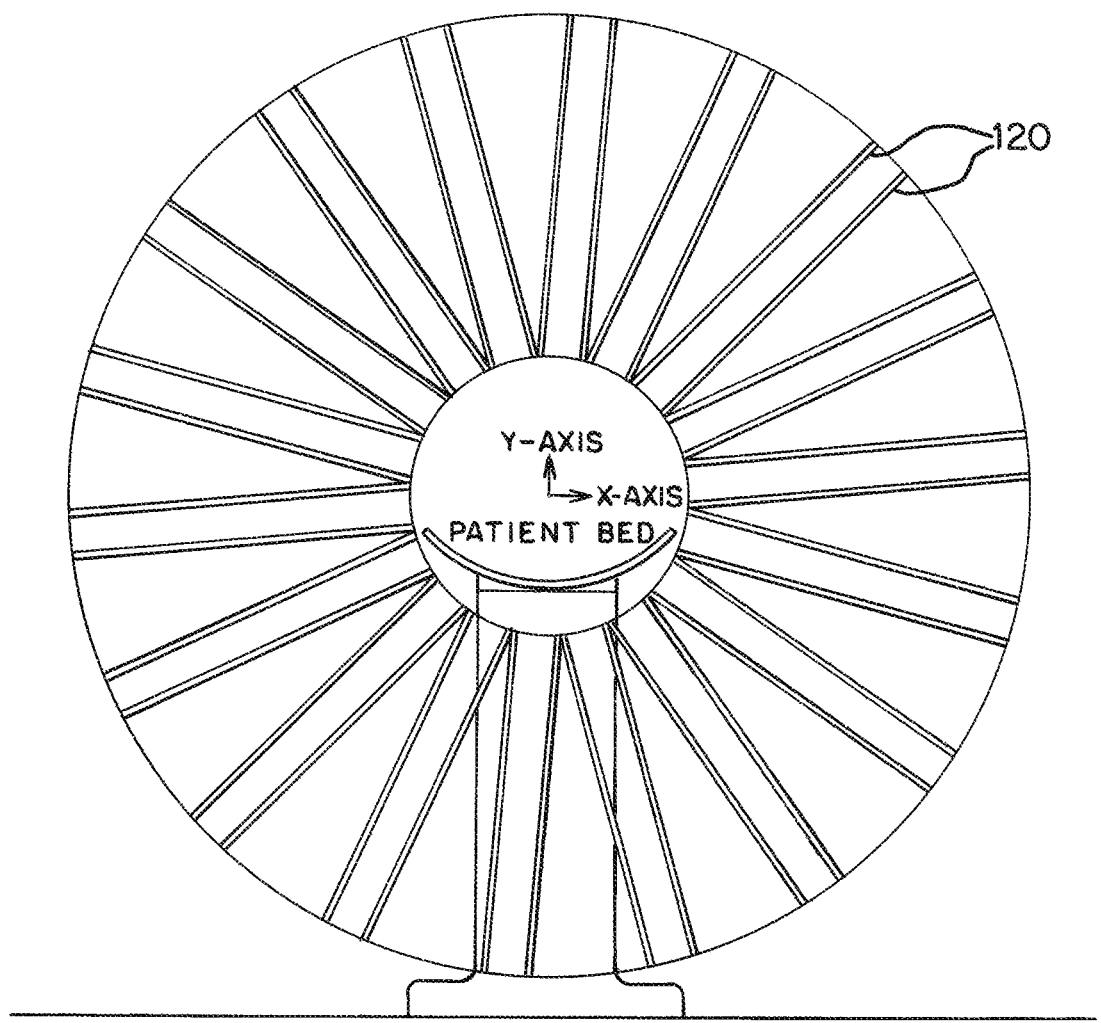
FIG. 12 is a cross-section view of one embodiment of tracks for an adaptive Compton camera.
Figure 16A:
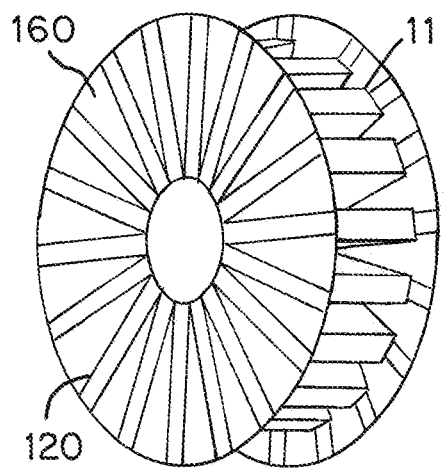
FIGS. 16A and 16B show modules of a Compton camera connected with guide planes.
Figure 16B:
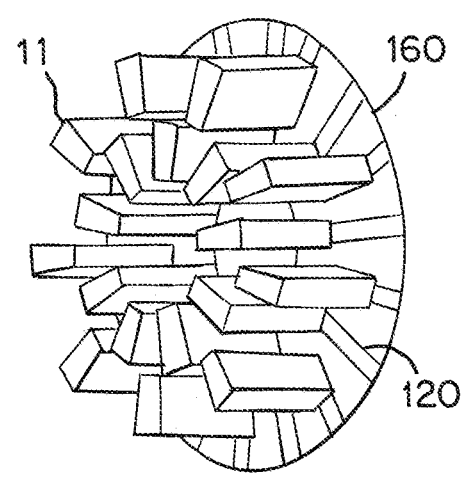

FIG. 12 shows one embodiment of guides 120. The guides 120 are channels, bars, pinions, racks, chain guides, or other structure for limiting or guiding the motion of the detectors 12, 13 along radial lines extending perpendicularly from the isocenter or a longitudinal axis through the patient space. In alternative embodiments, the guides 120 may be along other lines, such as offset from the radial. While shown as parallel lines, the guides 120 may be plates, cylinders, boxes, ducts, or other shapes for guiding the motion of the detectors 12, 13. FIGS. 16A and 16B shows the guides as part of two guide planes 160. The guides 120 in the guide planes 160 guide movement of the modules 11.

The motor 114 moves the detectors 12, 13 to be closer and/or further away from the patient bed 60 and patient space. In one embodiment, the guides 120 define the inner and outer extents of the possible positions. For example, the detectors 12, 13 may be positioned up to the ends of the guides 120. Blocks or motor control may be used to limit position. In another embodiment, the guides 120 include a telescoping component allowing one or more of the detectors 12, 13 to extend beyond an end of the guide 120. The control processor 112 or physical structure may be used to limit which scatter detectors 12 move closer where the scatter detectors 12 may collide if extended at the same time.

Each detector 12, 13 slides on a respective set of guides 120 in an XY plane (e.g., guide plane 160 orthogonal to a patient longitudinal axis and/or the isocenter of the imaging system). Each detector 12, 13 is positioned along a z-axis (i.e., radial orthogonal to the isocenter). The scatter and catcher layers may be translated axially in other embodiments.

The guides 120 may be carbon or other material generally transparent to photons. The motor 114 is positioned behind the catcher detectors 13 relative to the patient space to avoid interfering with photons.

FIG. 11 shows the scatter detectors 12 as having two positions relative to the patient space. The motor 114 moves the scatter detector 12 to one of the two positions. The guides 120 may limit the position. Similarly, the catcher detectors 13 have three positions relative to the patient space. The motor 114 moves the catcher detectors 13 to one of the three positions. The guides 120 may limit the position. In alternative embodiments, additional positions are provided or any position along a range of the guide 120 may be used.

The absolute number of scattered photons is increased by reducing the distance between the scatter detector 12 and the imaging object, thus increasing the solid angle $\Omega$. For smaller imaging objects, the scatter detector 12 may be placed closer to the isocenter. The same is not true for larger imaging objects. The sensitivity ($) of the adaptive Compton-camera is also increased by reducing the distance between the catcher detector 13 and the scatter detector 12, thus increasing the solid angle $\Omega$. Reducing the distance between the catcher detector 13 and the scatter detector 12 degrades image quality (IQ). Increasing the distance between the scatter detector 12 and the catcher detector 13 improves the image quality (IQ), while reducing the distance improves the sensitivity ($).

Figure 13:
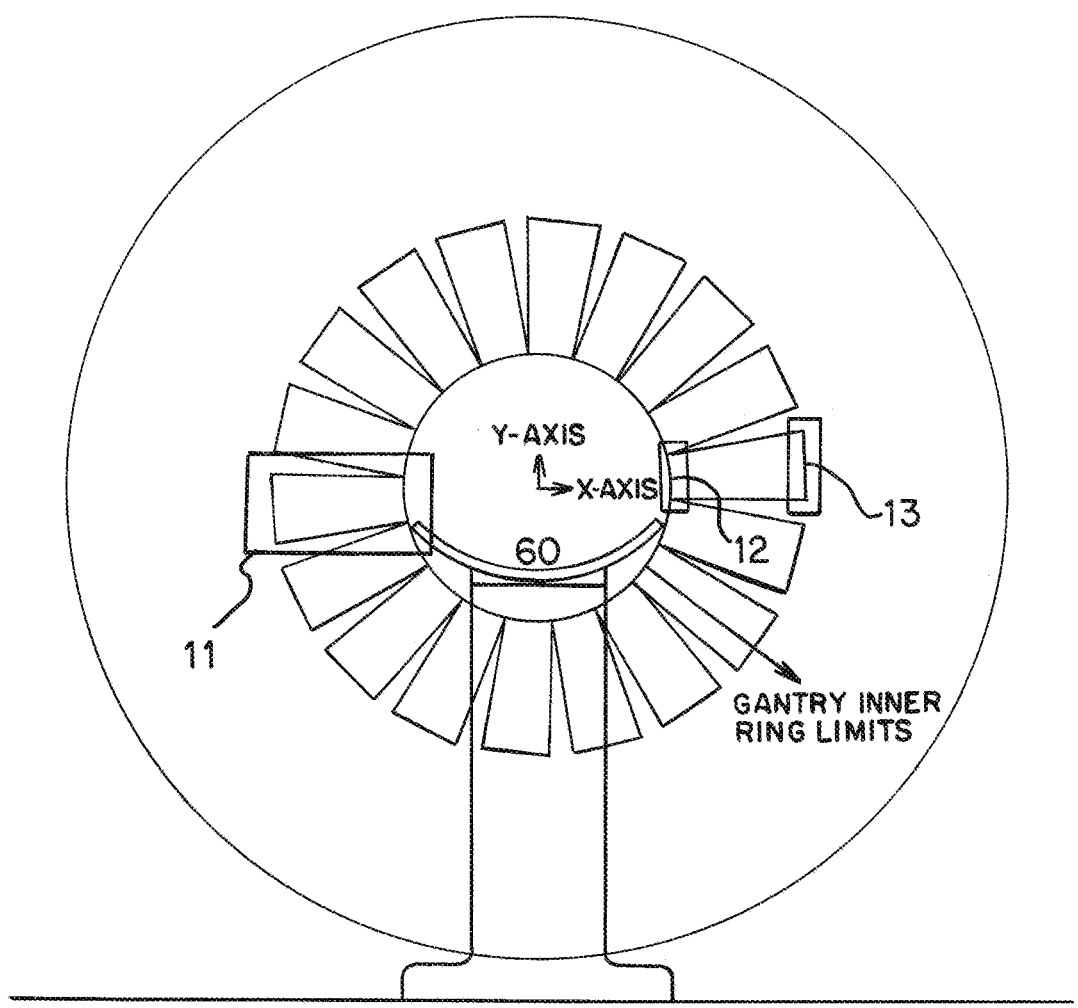
FIGS. 13 and 14 show modules of a Compton camera in different positions relative to the patient bed and patient space.
Figure 14:
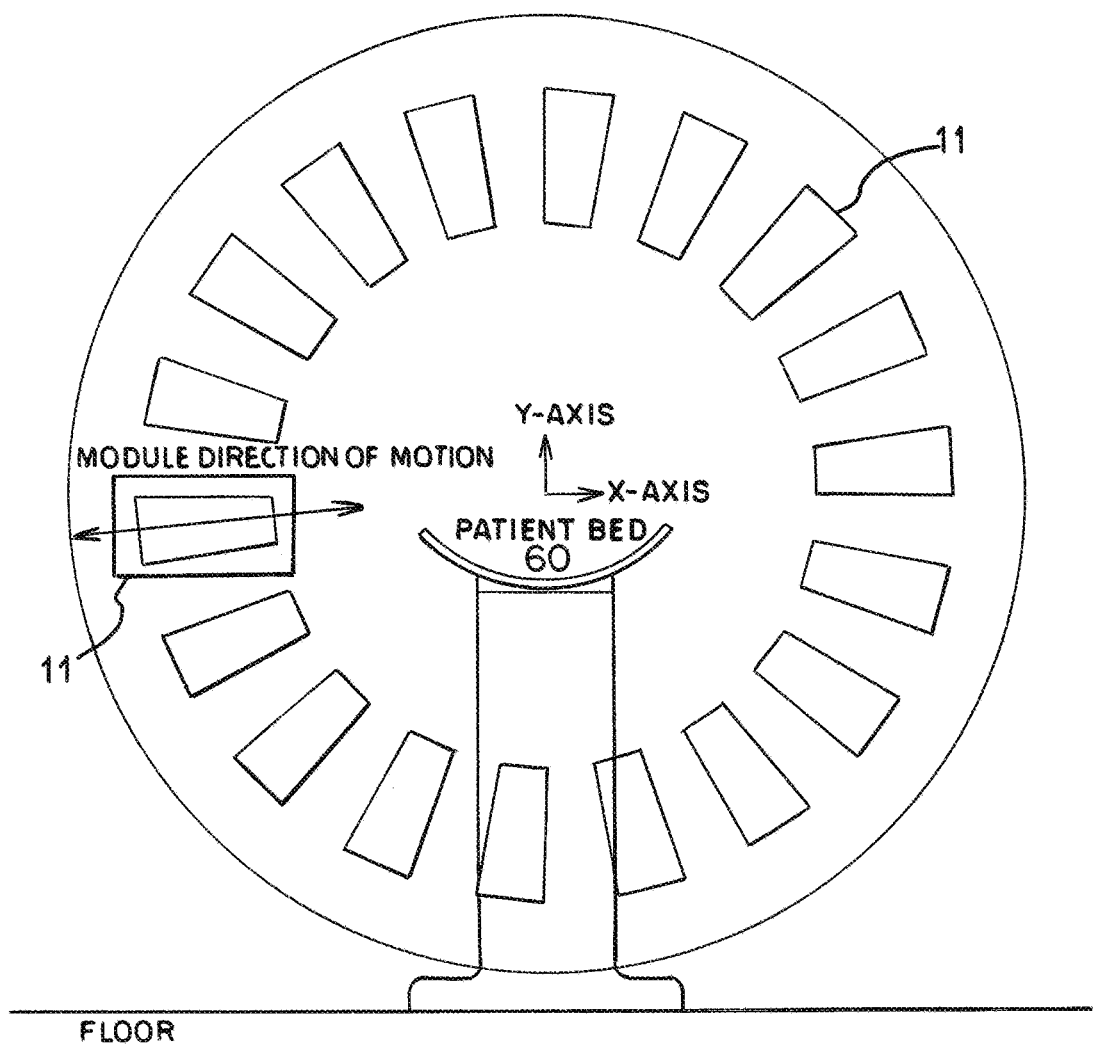

FIGS. 13 and 14 show one embodiment of the adaptive Compton camera. The modules 11 each include a scatter detector 12 and a catcher detector 13. The catcher detector 13 is at a fixed distance away from the scatter detector 12 within each module 11. The motor 114 connects with and moves the module 11 along the guides 120. The modules 11 are moved closer to or further away from the patient space, so the scatter detector 12 and the catcher detector 13 move together. The ring or partial ring of modules 11 on the gantry may be moved from an inner most position of FIG. 13 to an outer most position represented by the outer ring. While FIGS. 13 and 14 show the modules 11 all moved to a same distance away from the patient space, different modules 11 may be moved by different amounts and/or positioned at different depths relative to the isocenter or patient space. Alternatively, all modules 11 are connected to the singular motor 114 to move a same distance. FIG. 14 shows an arrow over one of the modules 11 representing the availability to move the module 11 further inward or outward.

In other embodiments, the scatter detector 12 or catcher detector 13 are moveable while the other detector (13, 12) does not move (i.e., is fixed in z-axis position). In yet other embodiments, the scatter detector 12 and catcher detector 13 move independently of each other. The scatter and catcher detectors 12, 13 may move within the module 11 and/or the modules 11 are moveable.

Figure 15:
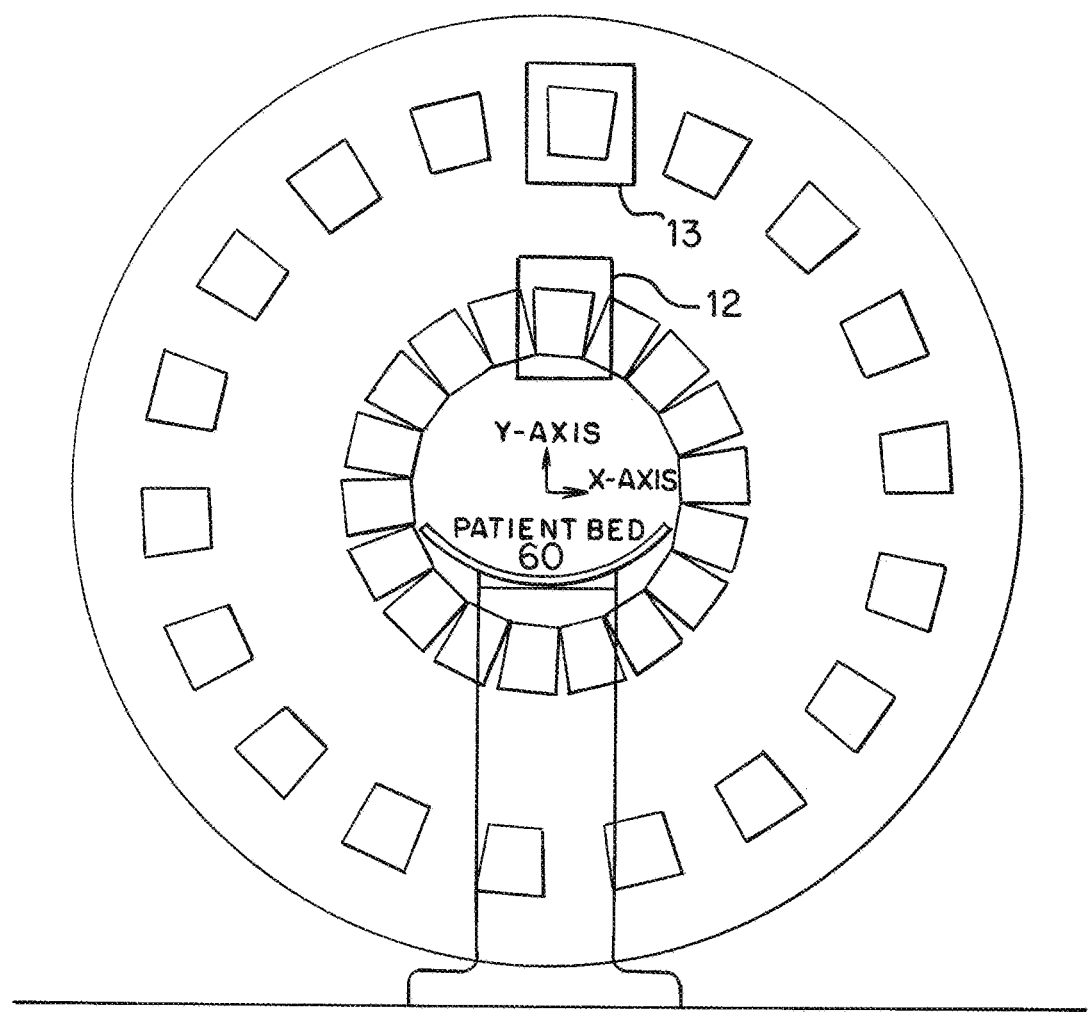
FIG. 15 shows the scatter and catcher detectors in an independently moveable arrangement.

FIG. 15 shows one embodiment where the scatter detector 12 and the catcher detector 13 are independently moveable relative to the patient bed 60 or patient space. These detectors 12, 13 may be within modules 11, such as pairs of detectors 12, 13 sharing a module housing or framework while being moveable independent of each other. Alternatively, the modules 11 are separated into one housing or framework for the scatter detector 12 and another housing or framework for the catcher detector 13. In other embodiments, the scatter and catcher detectors 12, 13 are not part of modules 11, but are independently moveable to expand or contract scatter and catcher layers separately.

By providing for independent movement, the scatter detectors 12 may be at an inner most position allowed by the guides 120 and/or patient, and the catcher detectors 13 may be an at outer most position allowed by the guides 120 and/or patient.

In moving the scatter detector 12 to reduce a distance of the scatter detector 12 from the patient based on an output of the sensor 110, different scatter detectors 12 may be at different distances from the isocenter. As shown in FIG. 11, different parts of the patient are different distances from the isocenter. Each scatter detector 12 is positioned relative to the patient based on the surface of the patient. Alternatively, all the scatter detectors 12 are positioned at a same distance from the isocenter where that distance minimizes the distance of the patient to the scatter detectors 12.

The catcher detectors 13 are all at a same distance from the isocenter, a same distance from respective scatter detectors, or at other distances. A combination of distances may be used for imaging a given patient, such as to optimize for multiple FOMs.

The control processor 112 is a processor, application specific integrated circuit, field programmable gate array, programmable logic controller, digital circuit, analog circuit, or combinations thereof. The control processor 112 controls operation of the motor 114. The control processor 112 receives one or more inputs, such as patient position information from the sensor 110, patient information (e.g., weight and height) from a user interface (e.g., user input device), and/or motor or detector position.

The control processor 112 is configured by hardware, firmware, and/or software to control the motor 114. The control processor 12 controls the motor 114 to set a distance between the scatter detector 12 and the catcher detector 13. The distance of the scatter detector 12 from the patient, patient space, or isocenter is controlled. The distance of a module 11 from the patient or patient space may be controlled. The control processor 112 causes the motor 114 to move the scatter detector 12, catcher detector 13, and/or module 11.

The position of the detectors 12, 13 adapts to a given examination. For one patient, the positions are set. For another patient, the positions are altered or different than used for the one patient. The control processor 112 causes the motor to alter the position or positions of the detectors 12, 13. Depending on the imaging application, size of the patient, position of the patient in the patient space, and/or other information, the position of the detectors 12, 13 is set. The motor 114 alters the current position to the set or desired location for Compton imaging of the patient.

The position is set based on any criteria. For example, the control processor 112 controls the motor 114 to move the scatter detector 12 to reduce a distance of the scatter detector 12 from the patient and controls the motor 114 to move the catcher detector 13 to a distance from the scatter detector 12.

In one embodiment, the control processor 112 controls the positions based on the FOM. The imaging task indicates the FOM. The position or positions may be different depending on the relative importance of various criteria, such as image quality and sensitivity. The user specifies the FOM. For example, the patient height, weight, body mass index, or other information results in a given FOM being more important. As another example, imaging technician inputs the FOM. In yet another example, a default FOM based on the imaging application or patient characteristics is used.

The control processor 112 determines the contour of the imaging object and/or distance of each scatter detector from the patient. The FOM is maximized accordingly. The absolute number of scattered photons is increased by reducing the distance between the scatter layer and the imaging object, thus increasing the solid angle $\Omega$. The scatter detectors 12 are positioned to minimize the distance from the patient with or without any constrains, such as a maintaining a given distance for patient comfort. For smaller imaging objects, the scatter layer may be place closer to the isocenter. The same is not true for larger imaging objects. Similarly, scatter detectors 12 of different modules 11 may be positioned different distances from the isocenter but a same distance away from the patient.

The sensitivity ($) of the adaptive Compton-camera is increased by reducing the distance between the catcher layer and the scatter layer, thus increasing the solid angle $\Omega$. Reducing the distance between the catcher layer and the scatter layer degrades image quality (IQ). By increasing the distance between the scatter layer and the catcher layer, the image quality (IQ) improves, while reducing the distance improves the sensitivity ($). In this 'adaptive' scenario, the specified FOM is used to determine the position of the catcher detector 13. For example, the FOM is sensitivity, so the catcher detector 13 is positioned to be close to the scatter detector 12, such as within 10 cm. As another example, the FOM is image quality, so the catcher detector 13 is positioned to be further from the scatter detector 12, such as over 10 cm (e.g., 20-70 cm). The system senses the contour of the imaging object and adapts accordingly to maximize the FOM.

The FOM may be indication of a single criterion of importance. Alternatively, the FOM is a relative weighting. Intermediate positioning of the catcher detectors 13 from the scatter detectors 12 may be used based on the relative importance of sensitivity to image quality. In other embodiments, different modules 11 use different relative weightings or FOM to provide Compton event detection based on different relative positions of the detectors 12, 13 by module 11 in the same scan of a same patient. In yet other embodiments, the relative position of the detectors 12, 13 to each other and/or the isocenter changes over time during a same scan, resulting in detecting events with different FOM at different times.

The Compton processor 19 (e.g., image processor) is configured to generate a Compton image from Compton events detected from the scatter and catcher detectors 12, 13. The electronics of the modules 11 or other electronics output events detected from the detectors 12, 13. The location, energy, and time of the events are received by the Compton processor 19. These events are paired using the location, energy, and/or time. Based on the pairing, location, and energy, an angle of incidence of the emission from the patient onto the scatter detector 12 is determined. The angle may be expressed probabilistically, such as a cone of incidence. Using reconstruction from many detected Compton events and the angle of incidence, a spatial distribution in patient or object space of the emissions is determined. A Compton image is rendered from the spatial distribution.

The Compton processor 19 is configured to perform digital collimation. Once events are paired, the angle of the scatter from the scatter detector 12 for a given event is determined. The relationship of energy and angle and the positions of the paired events indicates the angle of the scatter photon. Compton events may be rejected based on the angle, such as applying one or more scatter angle thresholds. The Compton image is generated from the Compton events that are not rejected. In other embodiments, digital collimation is not used.

Figure 17A:
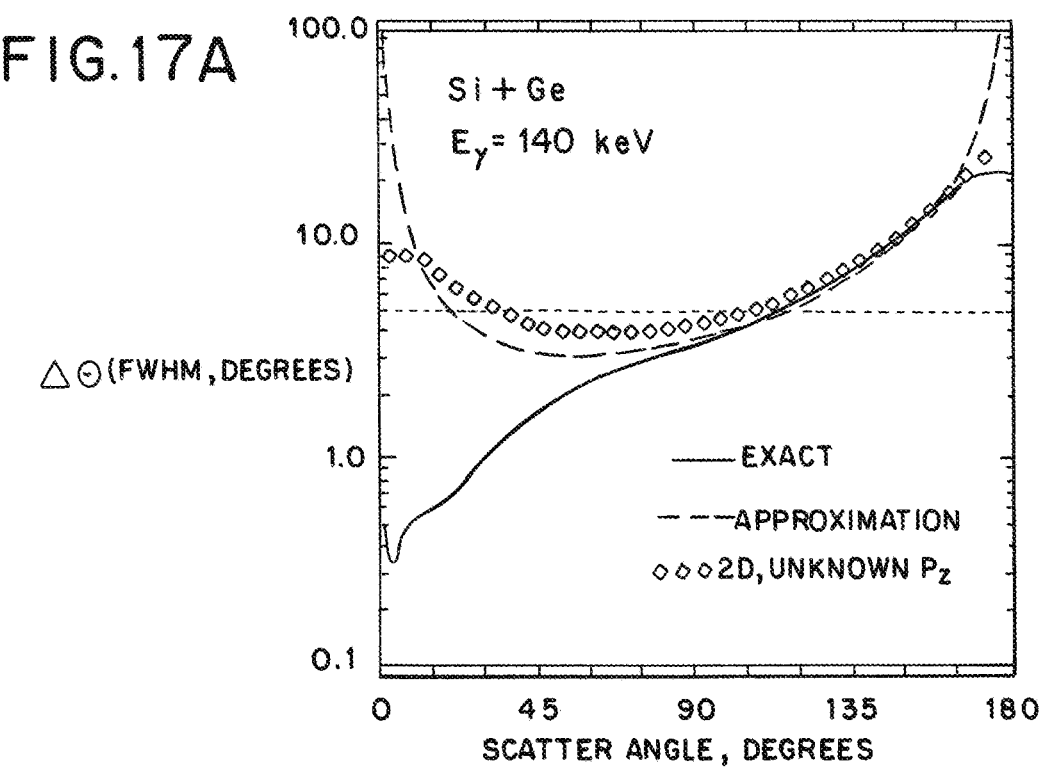
FIG. 17A shows an example graph of full width, half maximum (FWHM) by scatter angle for Compton imaging.
Figure 17B:
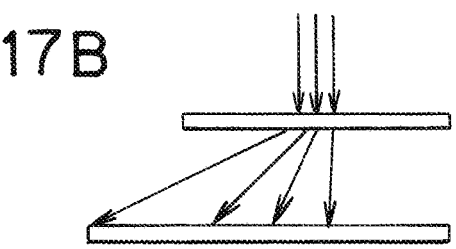
FIG. 17B shows example scatter angles.

FIG. 17A shows angular uncertainties in the Compton angle as a function of Compton angle. Compton events with some scatter angles may result in worse image quality. For example, the FWHM of a back projected cone is to be at a desired level, such as represented by the horizontal dashed line. The FWHM for a given Compton event is above or below the desired FWHM based on the scatter angle. For example, angles between 40 degrees and 120 degrees provide information with sufficient FWHM. FIG. 17B shows different scatter angles given emissions orthogonal to the scatter detector. Compton events for lesser (e.g., less than 40 degrees) and/or greater (e.g., greater than 120 degrees) scatter angles are not used (i.e., rejected by digital collimation). The remaining Compton events are used to generate the Compton image.

In one example, a CZT scatter detector 12 and CZT catcher detector 13 have a 30 cm distance between scatter and catcher layers with a 70 cm bore diameter. A PSF with FWHM<40.0 mm is produced by rejecting events with Compton angle greater than ~40°. Other thresholds may be used.

Referring again to FIG. 11, the display 22 is configured to display the Compton image. Using the non-rejected events, a Compton image with a balanced sensitivity and image quality is provided. The adaptation results in an image more diagnostically useful for a given patient and/or examination.

Figure 18:
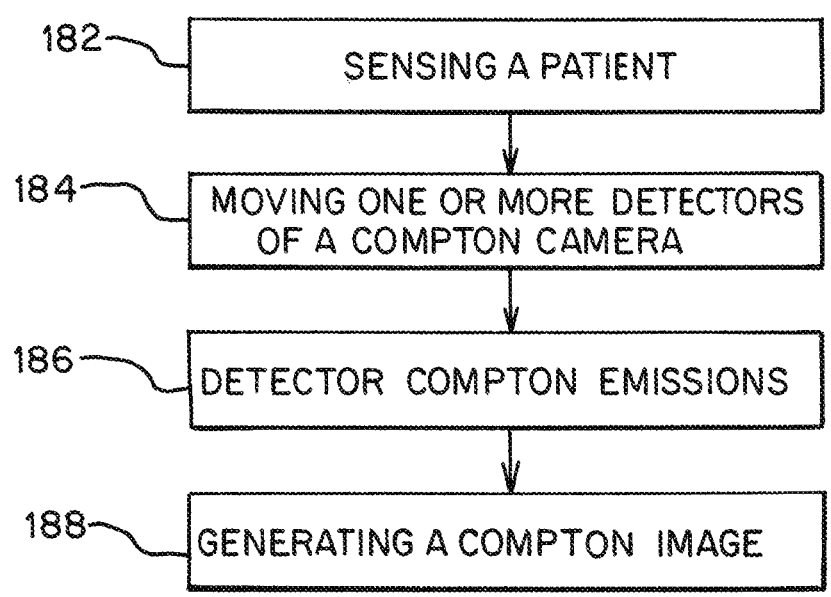
FIG. 18 is a flow chart diagram of an example embodiment of a method for Compton imaging.

FIG. 18 is a flow chart diagram of one embodiment of a method for medical imaging with a Compton camera. The method is implemented using the adaptive Compton camera of FIGS. 11-16B. Other adaptive Compton cameras able to change a position of one or more detectors used in the Compton camera may be used.

The acts are performed in the order shown or another order. Additional, different, or fewer acts may be provided. For example, the patient is not sensed in act 182. Instead, the catcher detector is moved relative to the scatter detector without the scatter detector being moved based on the patient position or with the scatter detector being moved based on patient weight rather than sensing. As another example, an image is not generated in act 188. The image is stored for later viewing.

In act 182, a sensor senses a patient. The outer surface of the patient is sensed relative to an iso-center, bed, and/or scatter detectors. The patient is sensed to allow positioning of the scatter detector or detectors within a threshold distance from the patient.

In act 184, one or more detectors of a Compton camera are moved. The detector or detectors are moved towards or away from the patient. Based on a FOM, examination type, and/or other information, the detector or detectors are moved.

In one embodiment, the scatter detector or detectors are moved by a motor and control processor based on an output of the sensing of the patient. The scatter detector or detectors are moved to be within a threshold distance from an outer surface of the patient nearest to the respective scatter detector. FIG. 11 shows an example where some scatter detectors are closer to the isocenter than other scatter detectors based on the outer surface of the patient.

Additionally or alternatively, the catcher detector or detectors are moved by a motor and control processor. Based on the examination type, a FOM, energies of the radioisotope involved, and/or other criteria, the catcher detector or detectors are moved relative to the isocenter, patient, and/or scatter detector or detectors. For example, the scatter detectors are positioned to be a given distance from the patient. The catcher detectors are then positioned to be a distance from the scatter detectors where the distance is based on a FOM or other information.

In act 186, the scatter and catcher detectors detect events. Gamma rays or photons emitted from the patient may interact with the scatter detector. These scatter events are detected. A resulting scatter photon is emitted and may interact with the catcher detector. The interaction in the catcher detector is detected.

The detected Compton events are paired. The paired Compton events are used to indicate an angle of incidence, such as a cone of probability, of the emission from the patient at the scatter detector. The Compton events may be digitally collimated based on the scatter angle.

The scatter and catcher detectors detect the events as positioned. During a scan of the patient, the detectors are maintained in the same position to detect. Alternatively, one or more detectors are moved during the same scan of the same patient.

In act 188, the paired Compton events maintained after any digital collimation are used to reconstruct a spatial distribution of the emissions from the patient. The sources of the emissions are estimated using the angles of incidence, locations, and counts of the Compton events. An image may be generated from the spatial distribution, such as a three-dimensional rendering or a cross-section planar image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A Compton camera for medical imaging, the Compton camera comprising:
a patient bed;
modules each having a scatter detector and a catcher detector, the modules positioned to receive emissions from a patient on the patient bed; and
a motor connected, for each of the modules, with the scatter detector, the catcher detector, both the scatter detector and the catcher detector, or that module, the motor configured to move the scatter detector, the catcher detector, both the scatter detector and the catcher detector, or that module closer or further from the patient bed.

2. The Compton camera of claim 1 wherein the scatter detector is at a fixed distance from the catcher detector, and wherein the motor is configured to move the scatter detector and the catcher detector together.

3. The Compton camera of claim 1 wherein the scatter detector is moveable relative to the catcher detector, and wherein the motor is configured to move the scatter detector without moving the catcher detector.

4. The Compton camera of claim 1 wherein the catcher detector is moveable relative to the scatter detector, and wherein the motor is configured to move the catcher detector without moving the scatter detector.

5. The Compton camera of claim 1 wherein the scatter detector and the catcher detector are independently moveable relative to the patient bed.

6. The Compton camera of claim 1 further comprising a sensor configured to sense a patient on the patient bed, wherein the motor is configured to move the scatter detector to reduce a distance of the scatter detector from the patient based on an output of the sensor.

7. The Compton camera of claim 1 further comprising a control processor configured to control the motor to set a distance between the scatter detector and the catcher detector based on a figure-of-merit balancing a sensitivity and an image quality.

8. The Compton camera of claim 7 wherein the control processor is further configured to control the motor to move the scatter detector to reduce a distance of the scatter detector from the patient and to control the motor to move the catcher detector to a distance from the scatter detector based on the figure-of-merit balancing the sensitivity and the image quality.

9. The Compton camera of claim 1 wherein the modules form part of a ring or a partial ring around the patient bed.

10. The Compton camera of claim 1 further comprising:
an image processor configured to generate a Compton image from Compton events formed from paired events in the scatter detector and the catcher detector; and
a display configured to display the Compton image.

11. The Compton camera of claim 1 further comprising an image processor configured to reject Compton events based on an angle threshold and generate a Compton image from non-rejected Compton events.

12. A medical imaging system comprising:
solid-state detector modules, each solid-state detector module having a scatter detector and a catcher detector;
a motor connected with the scatter detector, the catcher detector, or both the scatter detector and the catcher detector of one of the solid-state detector modules; and
a control processor configured to control the motor to alter a position of the scatter detector, the catcher detector, or both the scatter detector and the catcher detector relative to an isocenter of a patient space.

13. The medical imaging system of claim 12 further comprising a position sensor configured to sense a patient in the patient space, wherein the control processor is configured to alter the position of the scatter detector based on a sensed position of the patient from the position sensor.

14. The medical imaging system of claim 12 wherein the control processor is further configured to alter the position of the scatter detector and alter the position of the catcher detector such that a distance between the scatter detector and the catcher detector is altered.

15. The medical imaging system of claim 12 wherein the control processor is further configured to alter the position of the scatter detector, the catcher detector, or both the scatter detector and the catcher detector based on a relative selection between a sensitivity and an image quality.

16. A method for medical imaging with a Compton camera, the method comprising:
   moving, by a motor, a detector of the Compton camera, the detector comprising a first module including a first scatter detector, a first catcher detector, or both the first scatter detector and the first catcher detector, and a second module including a second scatter detector and a second catcher detector;
   detecting, by the moved detector of the Compton camera of the first module and the second module emissions from a patient; and
   generating a Compton image from the detected emissions from the patient.

17. The method of claim 16 further comprising:
   sensing a patient;
   wherein moving the detector of the Compton camera comprises moving the detector of the Compton camera based on an output of the sensing of the patient.

* * * * *